(12) United States Patent
DeLuca et al.

(10) Patent No.: US 10,494,337 B2
(45) Date of Patent: Dec. 3, 2019

(54) (20S)-1-α,25-DIHYDROXY-24,24-DIFLUORO-19-NOR-VITAMIN D$_3$ ANALOGS AND THEIR PHARMACEUTICAL USES

(71) Applicant: Wisconsin Alumni Research Foundation, Madison, WI (US)

(72) Inventors: Hector F. DeLuca, Deerfield, WI (US); Agnieszka Flores, Sun Prairie, WI (US); Lori A. Plum, Arena, WI (US); Hazel Holden, Fitchburg, WI (US); James Thoden, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/165,884

(22) Filed: May 26, 2016

(65) Prior Publication Data
US 2016/0347710 A1 Dec. 1, 2016

Related U.S. Application Data

(60) Provisional application No. 62/166,494, filed on May 26, 2015.

(51) Int. Cl.
C07C 401/00 (2006.01)
C07F 7/18 (2006.01)

(52) U.S. Cl.
CPC .......... *C07C 401/00* (2013.01); *C07F 7/1804* (2013.01)

(58) Field of Classification Search
CPC ................................ C07C 401/00; C07F 7/18
See application file for complete search history.

(56) References Cited

FOREIGN PATENT DOCUMENTS

WO 2013180880 A1 12/2013
WO 2013180882 A1 12/2013

OTHER PUBLICATIONS

Akiyoshi-Shibata, M.; Sasaki, T.; Ohyama, Y.; Noshiro, M.; Okuda, K.; Yabusaki, Y. Further oxidation of hydroxycalcidiol by calcidiol 24-hydroxylase. A study with the mature enzyme expressed in *Escherichia coli*. Eur J. Biochem. 1994, 224, 335-343.
Barton, D. H. R.; Jang, D. O.; Jaszberenyi, J. Cs. The invention of radical reactions. Part XXIX. Radical mono- and dideoxygenations with silanes. Tetrahedron 1993, 49, 2793-2804.
Beckman, M. J.; Tadikonda, P.; Werner, E.; Prahl, J.; Yamada, S.; DeLuca, H. F. Human 25-hydroxyvitamin D3-24-hydroxylase, a multicatalytic enzyme. Biochemistry 1996, 35, 8465-8472.
Bouillon, R.; Okamura, W. H.; Norman, A. W. Structure-function relationships in the vitamin D endocrine system. Endocr. Rev., 1995, 16, 200-257.
Chiellini, G.; Grzywacz, P.; Plum, L. A.; Barycki, R.; Clagett-Dame, M.; DeLuca, H. F. Synthesis and biological properties of 2-methylene-19-nor-25-dehydro-1□-hydroxyvitamin D3-26,26-lactones□weak agonists. Bioorg. Med. Chem. 2008, 16, 8563-8573.
Corradino, R.; DeLuca, H.; Tanaka, Y.; Ikekawa, N.; Kobayashi, Y.; A Fluorinated Vitamin D3 Analog with Biopotency Greater than 1a, 25-Dihydroxy Vitamin D3. Biochemical and Physical Research Communications. 1980, 96, 1800-1803.
De Luca, H. F. Overview of general physiologic features and functions of vitamin D. Am. J. Clin. Nutr. 2004, 80 (suppl), 1689S-1696S.
Flack, H. D. On enantiomorph—polarity estimation. Acta Cryst. A 1983, 39, 876-881.
Flores, A.; Siciński, R. R.; Grzywacz, P.; Thoden, J.; Plum, L.; Clagett-Dame, M.; DeLuca, H.F. A 20S combined with a 22R configuration markedly increases both in vivo and in vitro biological activity of 1?,25-dihydroxy-22-methyl-2-methylene-19-norvitamin D3. J. Med. Chem. 2012, 55, 4353-4366.
Flores, A.; Massarelli, I.; Thoden, J.; Plum, L.; DeLuca, H.; A Methylene Group on C-2 of 24,24-Difluoro-19-nor-1a, 25-dihydroxyvitamin D3 Markedly Increases Bone Calcium Mobilization in Vivo. Med. Chem. 2015, 58, 9731-9741.
Fürstner, A. Recent advancements in the Reformatsky reaction. Synthesis 1989, 571-590.
Głębocka, A.; Siciński, R. R.; Plum, L. A.; Clagett-Dame, M.;DeLuca, H. F. New 2-alkylidene 1?,25-dihydroxy-19-norvitamin D3 analogues of high intestinal activity: synthesis and biological evaluation of 2-(3'-alkoxypropylidene)- and 2-(3'-hydroxypropylidene) derivatives. J. Med. Chem. 2006, 49, 2909-2920.
Hallinan, E. A.; Fried, J. 2,2-difluoro-3-hydroxyesters by Reformatskii reaction. Tetrahedron Lett. 1984, 25, 2301-2302.
Ikeda, M., Matsumura, H., Sawada, N., Hashimoto, K., Tanaka, T., Noguchi, T., Hayashi, M. Synthesis and biological evaluations of C-23-modified 26,26,26,27,27,27-F6-vitamin D3 analogues. Bioorg. Med. Chem. 2000, 8, 1809-1817.
Inaba, Y.; Abe, E.; Okuno, S.; Nishizawa, Y.; Yukioka, K.; Otani, S.; Matsui-Yuasa, I.; Morisawa, S.; DeLuca, H. F.; Morii, H. Biological activity of fluorinated vitamin D analogs at C-26 and C-27 on human promyelocytic leukemia cells, HL-60. Arch. Biochem. Biophys. 1987, 258, 421-425.
Iwasaki, H.; Hosotani, R; Miyamoto, Y.; Nakano, Y. Stereoselective synthesis and structural establishment of (25S)-24,24-difluoro-1□,25,26-trihydroxyvitamin D3, a major metabolite of 24,24-difluoro-1□25-dihydroxy-vitamin D3. Tetrahedron 1998, 54, 14705-14724.
Jones, G.; Strugnell, S. A.; DeLuca, H. F. Current understanding of the molecular actions of vitamin D. Physiol. Rev. 1998, 78, 1193-1231.
Kensler, T. W.; Dolan, P. M.; Gange, S. J.; Lee, J-K.; Wang, Q.; Posner, G. H. Conceptually new deltanoids (vitamin D analogs) inhibit multistage skin tumorigenesis. Carcinogenesis 2000, 21, 1341-1345.
Kobayashi, Y., Taguchi, T., Mitsuhashi, S., Eguchi, T., Ohshima, E., Ikekawa, N. Studies on organic fluorine compounds. XXXIX. Studies on steroids. LXXIX. Synthesis of 1□,25-dihydroxy-26,26,26,27,27,27-hexafluorovitamin D3. Chem. Pharm. Bull. 1982, 30, 4297-4303.

(Continued)

*Primary Examiner* — Zohreh A Fay
(74) *Attorney, Agent, or Firm* — Quarles & Brady LLP

(57) ABSTRACT

Disclosed are 1α,25-dihydroxy-24,24-difluoro-2-methylene-19-nor-vitamin D analogs and their pharmaceutical uses. These new vitamin D analogs are 19-nor-vitamin D analogs having two fluorine atom substitutions at the 24 position (C-24) in the side chain and optionally having a 2-methylene substituent.

9 Claims, 15 Drawing Sheets

(56) References Cited

OTHER PUBLICATIONS

Konno, K.; Ojima, K.; Hayashi, T.; Takayama, H. An alternative and efficient synthesis of 24,24-difluoro-1□,25-dihydroxyvitamin D3. Chem. Pharm Bull. 1992, 40, 1120-1124.

Lythgoe, B.; Moran, T. A.; Nambudiry, M. E. N.; Ruston, S.; Tideswell, J.; Wright, P. W. Allylic phosphine oxides as precursors of dienes of defined geometry: synthesis of 3-deoxyvitamin D2. Tetrahedron Lett. 1975, 44, 3863-3866.

Lythgoe, B.; Nambudiry, M. E. N.; Tideswell, J. Direct total synthesis of vitamins D2 and D3. Tetrahedron Lett. 1977, 41, 3685-3688.

Lythgoe, B.; Moran, T. A.; Nambudiry, M. E. N.; Tideswell, J. Wright, P. W. Calciferol and its derivatives. Part 22. A direct synthesis of vitamin D2 and D3. J. Chem. Soc., Perkin Trans. 1 1978, 590-595.

Miyamoto, Y.; Shinki, T.; Yamamoto, K.; Ohyama, Y.; Iwasaki, H.; Hosotani, R.; Kasama, T.; Takayama, H.; Yamada, S.; Suda, T. 1□,25-dihydroxyvitamin D3-24-hydroxylase (CYP24) hydroxylates the carbon at the end of the side chain (C-26) of the C-24-fluorinated analog of 1□,25-dihydroxyvitamin D3. J. Biol. Chem. 1997, 272, 14115-14119.

Molander, G. Application of lanthanide reagents in organic synthesis. Chem. Rev. 1992, 92, 29-68.

Molander, G. A.; Harris, C. R. Sequencing reactions with samarium (II) iodide. Chem. Rev. 1996, 96, 307-338.

Ocampo, R.; Dolbier, Jr. W. R. The Reformatsky reaction in organic synthesis. Recent advances. Tetrahedron 2004, 60, 9325-9374.

Ojima I. Fluorine in medicinal chemistry and chemical biology. John Wiley & Sons, Inc. 2009.

Peleg, S.; Petersen, K. S.; Suh, B. C.; Dolan, P.; Agoston, E. S.; Kensler, T. W.; Posner, G. H. Low-calcemic, highly antiproliferative, 1-difluoromethyl hybrid analogs of the natural hormone 1□,25-dihydroxyvitamin D3: design, synthesis, and preliminary biological evaluation. J. Med. Chem. 2006, 49, 7513-7517.

Posner, G. H.; Lee, J. K.; Wang, Q.; Peleg, S.; Burke, M.; Brem, H.; Dolan, P.; Kensler, T. Noncalcemic, antiproliferative, transcriptionally active, 24-fluorinated hybrid analoges of the hormone 1□,25-dihydroxyvitamin D3. Synthesis and preliminary biological evaluation. J. Med. Chem. 1998, 41, 3008-3014.

Posner, G. H.; Wang, Q.; Han, G.; Lee, J. K.; Crawford, K.; Zand, S.; Brem, H.; Peleg, S.; Dolan, P.; Kensler, T. Conceptually new sulfone analogues of the hormone 1□,25-dihydroxyvitamin D3: synthesis and preliminary biological evaluation. J. Med. Chem. 1999, 42, 3425-3435.

Posner, G. Low-calcemic vitamin D analogs (deltanoids) for human cancer prevention. J. Nutr. 2002, 3802S-3803S.

Posner, G. H.; Woodard, B. T.; Crawford, K. R.; Peleg, S.; Brown, A. J.; Dolan, P. Kensler, T. W. 2,2-Disubstituted analogues of the natural hormone 1□,25-dihydroxyvitamin D3: chemistry and biology. Bioorg. Med. Chem. 2002, 10, 2353-2365.

Posner, G. H.; Kim, H. J.; Kahraman, M.; Jeon, H. B.; Suh, B. C.; Li, H.; Dolan, P.; Kensler, T. W. Highly antiproliferative, low-calcemic, side chain ketone analogs of the hormone 1□,25-dihydroxyvitamin D3. Bioorg. Med. Chem. 2005, 13, 5569-5580.

Shevde, N.K.; Plum, L. A.;Clagett-Dame, M.; Yamamoto, H.; Pike, J. W.; DeLuca, H. F. A potent analog of 1□,25-dihydroxyvitamin D3 selectively induces bone formation. Proc. Natl. Acad.Sci. U.S.A. 2002, 99, 13487-13491.

Siciński, R. R.; Prahl, J.; Smith, C.; DeLuca, H. F. New 1?,25-dihydroxy-19-norvitamin D3 compounds of high biological activity: synthesis and biological evaluation of 2-hydroxymethyl, 2-methyl, and 2-methylene analogues. J. Med. Chem. 1998, 41, 4662-4674.

Tanaka, Y., DeLuca, H., Kobayashi, Y., Ikekawa, N. 26,26,26,27,27,27-hexafluoro-1,25-dihydroxyvitamin D3: a highly potent, long-lasting analog of 1,25-dihydroxyvitamin D3. Arch. Biochem. Biophys. 1984, 229, 348-354.

Tavera-Mendoza, L. E.; Quach, T. D.; Dabbas, B.; Hudon, J.; Liao, X.; Palijan, A.; Gleason, J. L.; White, J. H. Incorporation of histone deacetylase inhibition into the structure of a nuclear receptor agonist. Proc. Natl. Acad. Sci. USA 2008, 105, 8250-8255.

Yamada, S.; Ohmori, M.; Takayama, H. Synthesis of 24,24-difluoro-25-hydroxyvitamin D3. Tetrahedron Lett. 1979, 21, 1859-1862.

International Search Report and Written Opinion of PCT/US2016/034392 dated Aug. 19, 2016.

International Preliminary Report on Patentability for PCT/US2016/034392 dated Dec. 7, 2017.

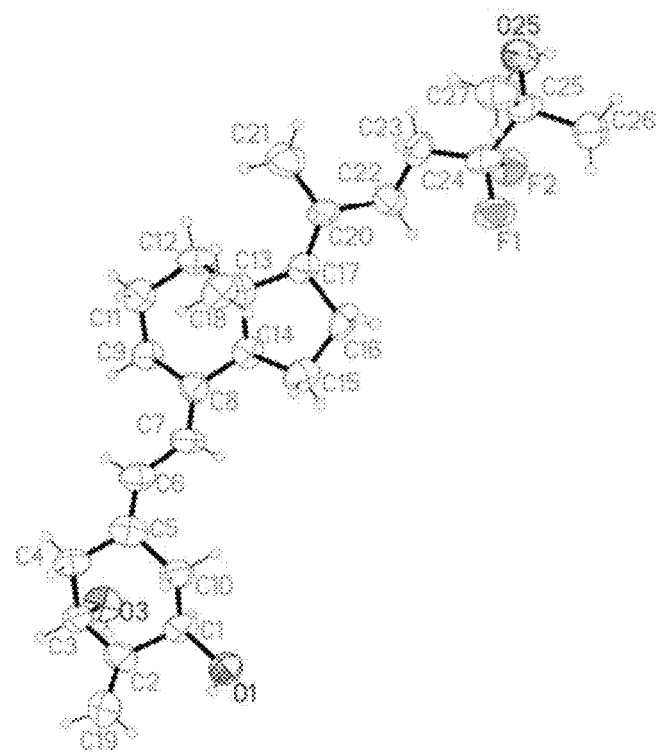
3 (20R) (F-24)
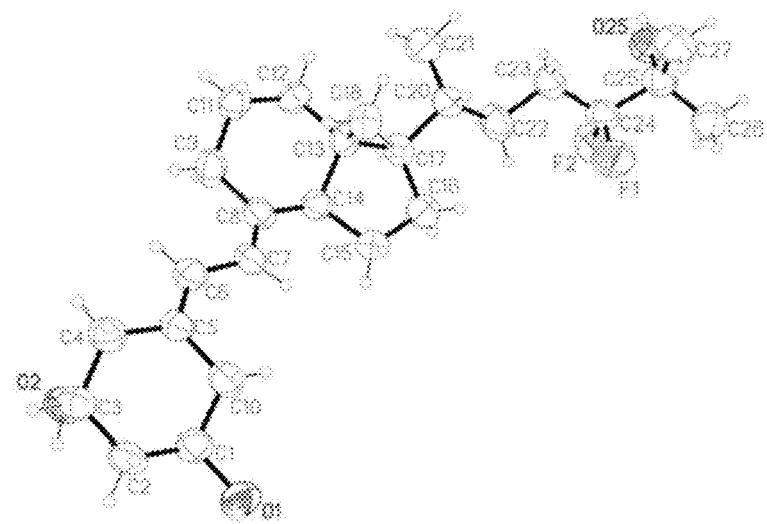
5 (20R) (24F$_2$-DM)
Figure 2

Figure 5. $^1$H NMR spectrum of the vitamin D analog 3 (F-24)

Figure 6. $^{13}$C NMR spectrum of the vitamin D analog 3 (F-24)

Figure 7. $^1$H NMR spectrum of the vitamin D analog 4 (DIF-24)

Figure 8. $^{13}$C NMR spectrum of the vitamin D analog 4 (DIF-24)

Figure 9. $^1$H NMR spectrum of the vitamin D analog 5 (24F2-DM)

Figure 10. $^{13}$C NMR spectrum of the vitamin D analog 5 (24F2-DM)

Figure 11. $^1$H NMR spectrum of the vitamin D analog 6 (DIF)

Figure 12. $^{13}$C NMR spectrum of the vitamin D analog 6 (DIF)

(20S)-1-α,25-DIHYDROXY-24,24-DIFLUORO-19-NOR-VITAMIN D₃ ANALOGS AND THEIR PHARMACEUTICAL USES

CROSS-REFERENCE TO RELATED PATENT APPLICATION

This application claims the benefit of priority to under 35 U.S.C. § 119(e) U.S. Provisional Application No. 62/166,494, filed on May 26, 2015, the content of which is incorporated herein by reference in its entirety.

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND

This invention relates to vitamin D compounds and their pharmaceutical uses. In particular, the invention relates to 1α,25-dihydroxy-24,24-difluoro-2-methylene-19-nor-vitamin D analogs and their pharmaceutical uses.

The biologically active metabolite of vitamin $D_3$, 1α,25-$(OH)_2D_3$ (i.e., the native hormone or "calcitriol") is best known for its regulation of calcium and phosphorus homeostasis, but it also plays a role in controlling other biological functions such as induction of cell differentiation or proliferation. The use of calcitriol in hyperproliferative disorders is limited by its calcemic effects, and therefore there is a continuing interest in chemically modified analogues of 1α,25-$(OH)_2D_3$ and their clinical applications.[1]

The native hormone undergoes chemical transformations in vivo, such as 23S- and 24R-hydroxylation catalyzed by CYP24A1 hydroxylase, oxidation of the 24-hydroxy group to a ketone, and cleavage of the C-23-C-24 bond of (23S)-23,25-dihydroxy-24-oxovitamin $D_3$.[2] By preventing or slowing this catabolic degradation, for instance by introducing fluorine atoms, analogues with a longer life-time that are more resistant to oxidation can be prepared.[3] The substitution of hydrogen atoms with fluorine atoms is dictated by physical and chemical properties. The high electronegativity of fluorine, its small size, the good overlap of the 2s or 2p orbitals with corresponding orbitals of carbon as well as the presence of three lone pairs of electrons mean that C—F bonds are always polarized from the sp³ carbon atom ($δ^+$) to the fluorine atom ($δ^-$). Because of the C—F bond's stability and the similar size of hydrogen and fluorine atoms, fluorinated vitamin D analogues have been prepared which exhibit slower catabolism degradation.[4,5]

Fluorine-substituted side-chain analogues were synthesized first in the early 1980s. The use of 24,24-difluoro-25-hydroxyvitamin $D_3$ was used to show that 24-hydroxylation is not required for the action of vitamin D.[6] Falecalcitriol (26,27-hexafluorocalcitriol) marketed for the treatment of hypocalcemia, rickets, and osteomalacia was found to be several times more potent then calcitriol both in vitro and in vivo systems, with a longer duration of its action in vivo.[7] Numerous other modifications on the fluorinated side chain (e.g., a double[8-10] and a triple[9] bonds, sulfone,[8] a carbonyl group,[10] oxetan[11]) as well as introduction of a fluorine atom on the A ring of vitamin $D_3$ have also been investigated.[12]

In addition to fluorination, the stereochemistry of vitamin D analogues also has been shown to affect biological activity. For example, the native hormone has (20R) stereochemistry, and it has been found that a 20-epimer analogue of 1α,25-$(OH)_2D_3$ having (20S) stereochemistry rather than (20R) stereochemistry exhibits increased biological activities. Furthermore, the position of the methylene group on the A ring of vitamin D analogues has been shown to affect biological activity. For example, the native hormone has a C-10 methylene group, and the combination of C-20 epimerization from 20R stereochemistry to 20S stereochemistry and replacement of the methylene group from the C-10 carbon to the C-2 carbon results in an analogue that exhibits increased bone synthesis activity and increased resorption activity (i.e., increased turnover activity).

Here, we now have found replacement of the C-10 methylene group to the C-2 carbon (i.e., "2-methylene substitution") markedly increases bone calcium mobilizing activity when the configuration of C-20 is in the R configuration in 24,24-difluoro-19-nor-1α,25-dihydroxyvitamin D compounds. However, when the C-20 is in the S configuration in 24,24-difluoro-19-nor-1α,25-dihydroxyvitamin D compounds, 2-methylene substitution has little or no effect on bone calcium mobilization activity.

SUMMARY

Disclosed are 1α,25-dihydroxy-24,24-difluoro-2-methylene-19-nor-vitamin D analogs and their pharmaceutical uses. These new vitamin D analogs are 19-nor-vitamin D analogs having two fluorine atom substitutions at the 24 position (C-24) in the side chain and optionally having a 2-methylene substituent.

Structurally these 1α,25-dihydroxy-24,24-difluoro-2-methylene-19-nor-vitamin D analogs are characterized by the general formula I shown below:

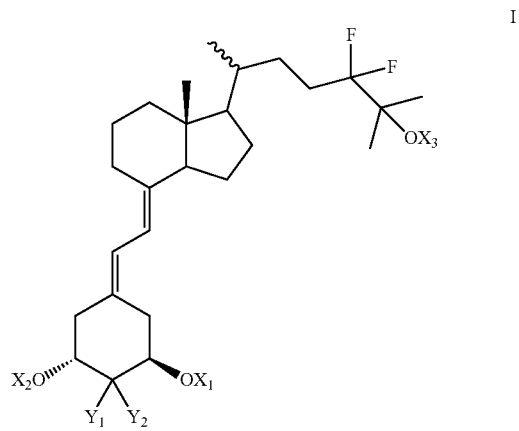

where $X_1$, $X_2$, and $X_3$, which may be the same or different; $X_1$, $X_2$, and $X_3$ are each selected from hydrogen or a hydroxy-protecting group; and $Y_1$ and $Y_2$ are hydrogen or together form a methylene group.

One disclosed compound is (20R)-1α,25-Dihydroxy-24,24-difluoro-2-methylene-19-norvitamin $D_3$ otherwise referred to herein as "F-24" and having a formula:

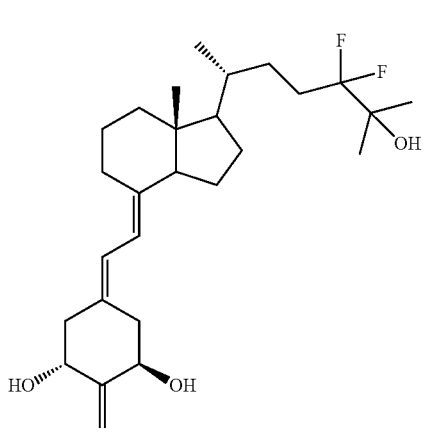 [SMILES: C=C1[C@H](O)CC(=C/C=C2\CCC[C@@]3(C)C2CCC3[C@H](C)CCC(F)(F)C(C)(C)O)C[C@H]1O]

Another disclosed compound is (20S)-1α,25-Dihydroxy-24,24-difluoro-2-methylene-19-norvitamin $D_3$ otherwise referred to herein as "DIF-24" and having a formula:

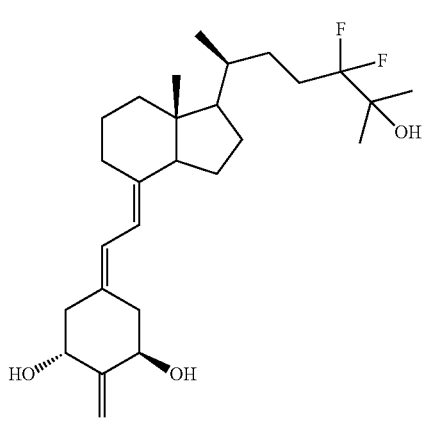 [SMILES: C=C1[C@H](O)CC(=C/C=C2\CCC[C@@]3(C)C2CCC3[C@@H](C)CCC(F)(F)C(C)(C)O)C[C@H]1O]

Another disclosed compound is (20R)-1α,25-Dihydroxy-24,24-difluoro-19-norvitamin $D_3$ otherwise referred to herein as "$24F_2$-DM" and having a formula:

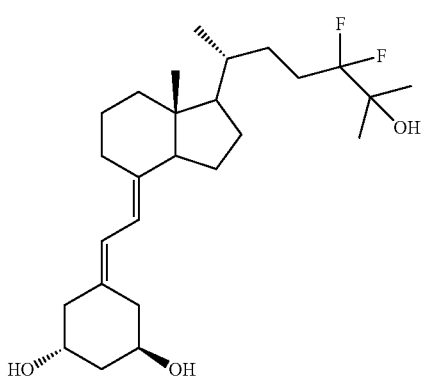 [SMILES: C[C@H](CCC(F)(F)C(C)(C)O)C1CCC2/C(=C/C=C3C[C@@H](O)C[C@H](O)C3)CCC[C@@]21C]

Another disclosed compound is (20S)-1α,25-Dihydroxy-24,24-difluoro-19-norvitamin $D_3$ otherwise referred to herein as "DIF" and having a formula:

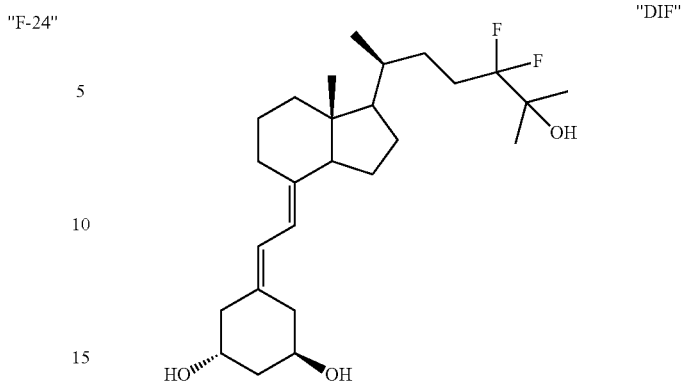

The disclosed compounds exhibit desirable and advantageous biological activities. First, the disclosed compounds bind to the vitamin D receptor (VDR) with similar activity as the native hormone (1α,25-$(OH)_2D_3$ aka "calcitriol"). However, all of the disclosed compounds are significantly more active in causing differentiation of the cancer cell line HL-60 than the native hormone. Also, all of the disclosed compounds are significantly more active in increasing transcription from the 24-hydroxylase gene promoter than the native hormone. The compounds also exhibit desirable and advantageous biological activities in regard to bone calcium mobilization and intestinal calcium transport.

Because of the desirable and advantageous biological activities of the disclosed compounds, the disclosed compounds may be utilized in methods for treating and/or preventing diseases or disorders associated with vitamin D activity in a patient in need thereof. In some embodiments, the compounds disclosed herein may be utilized in methods for treating and/or preventing bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. The disclosed compounds also may be administered in methods for increasing bone strength in a patient.

In other embodiments, the compounds disclosed herein may be utilized in methods for treating and/or preventing skin diseases, disorders, and conditions in a patient in need thereof. These may include, but are not limited to psoriasis, acne, lack of adequate skin firmness, lack of adequate dermal hydration, and insufficient sebum secretion.

In further embodiments, the compounds disclosed herein may be utilized in methods for treating and/or preventing cell proliferative diseases or disorders such as cancer in a patient in need thereof. These may include, but are not limited to leukemia, colon cancer, breast cancer, skin cancer, and prostate cancer.

In even further embodiments, the compounds disclosed herein may be utilized in methods for treating and/or preventing autoimmune diseases and disorders in a patient in need thereof. These may include, but are not limited to multiple sclerosis, diabetes mellitus, lupus, host versus graft reaction, and rejection of transplants.

In even further embodiments, the compounds disclosed herein may be utilized in methods for treating and/or preventing inflammatory diseases. These may include, but are not limited to rheumatoid arthritis, asthmas, and inflammatory bowel diseases. The compounds may be utilized specifically in methods of treating or preventing inflammatory bowel diseases that include Crohn's disease and ulcerative colitis.

In even further embodiments, the compounds disclosed herein may be utilized in methods for treating and/or preventing obesity, inhibiting adipocyte differentiation, inhibiting SCD-1 gene transcription, and/or reducing body fat.

In even further embodiments, the compounds disclosed herein may be utilized in methods for treating and/or preventing secondary hyperparathyroidism, for example, secondary hyperparathyroidism of renal osteodystrophy.

The disclosed compounds may be formulated in compositions such as pharmaceutical compositions. In some embodiments, pharmaceutical compositions may comprise the disclosed compounds (or pharmaceutically acceptable salts thereof) in a minimal dose of at least about 0.01, 0.05, 0.1, 0.5, 1.0, 5.0, 10.0, 50.0, 100.0, 500.0 or 1000.0 μg/gm of the composition. In other embodiments, pharmaceutical composition may comprise the disclosed compounds (or pharmaceutically acceptable salts thereof) in a maximal dose no greater than 1000.0, 500.0, 100.0, 50.0, 10.0, 5.0, 1.0, 0.1, 0.05 μg/gm of the composition, preferably from about 0.1 μg/gm to about 500 μg/gm of the composition. In other embodiments, the compositions may comprise the disclosed compounds within dose ranges having as end-points any of these disclosed doses (e.g., 0.01-1000.0 μg/gm of the composition). Minimal and/or maximal doses may be administered at any suitable frequency, such as daily, three times per week, weekly, or other frequencies.

The disclosed compounds may be administered at a minimal dose level for achieving therapy. In some embodiments, a minimal dose level for achieving therapy may be at least about 0.1, 0.25, 0.5, 1.0, 2.5, 5.0, 10.0, 12.5, 15.0, or 20.0 ng/kg body weight of the subject. The disclosed compounds may be administered at a maximal dose level for achieving therapy without resulting in an undesirable side effect such as hypercalcemia. In some embodiments, a maximal dose level may not exceed about 20.0, 15.0, 12.5, 10.0, 5.0, 2.5, 1.0, 0.5, 0.25, and 0.1 ng/kg body weight of the subject. Minimal and/or maximal dose levels may include dose level ranges having as end-points any of these discloses dose levels (e.g., 0.1-20.0 ng/kg body weight of the subject). Minimal and/or maximal dose levels may be administered at any suitable frequency, such as daily, three times per week, weekly, or other frequencies.

The disclosed compounds may be administered via any suitable route of administration. Suitable routes of administration may include but are not limited to topical, transdermal, oral, rectal, nasal, sublingual, or parenteral routes of administration.

BRIEF DESCRIPTION OF THE DRAWINGS

FIG. 2. ORTEP drawings derived from the single-crystal X-ray analysis of the vitamins 3 (F-24) and 5 (24F2-DM).

DETAILED DESCRIPTION OF THE INVENTION

Figure 1:
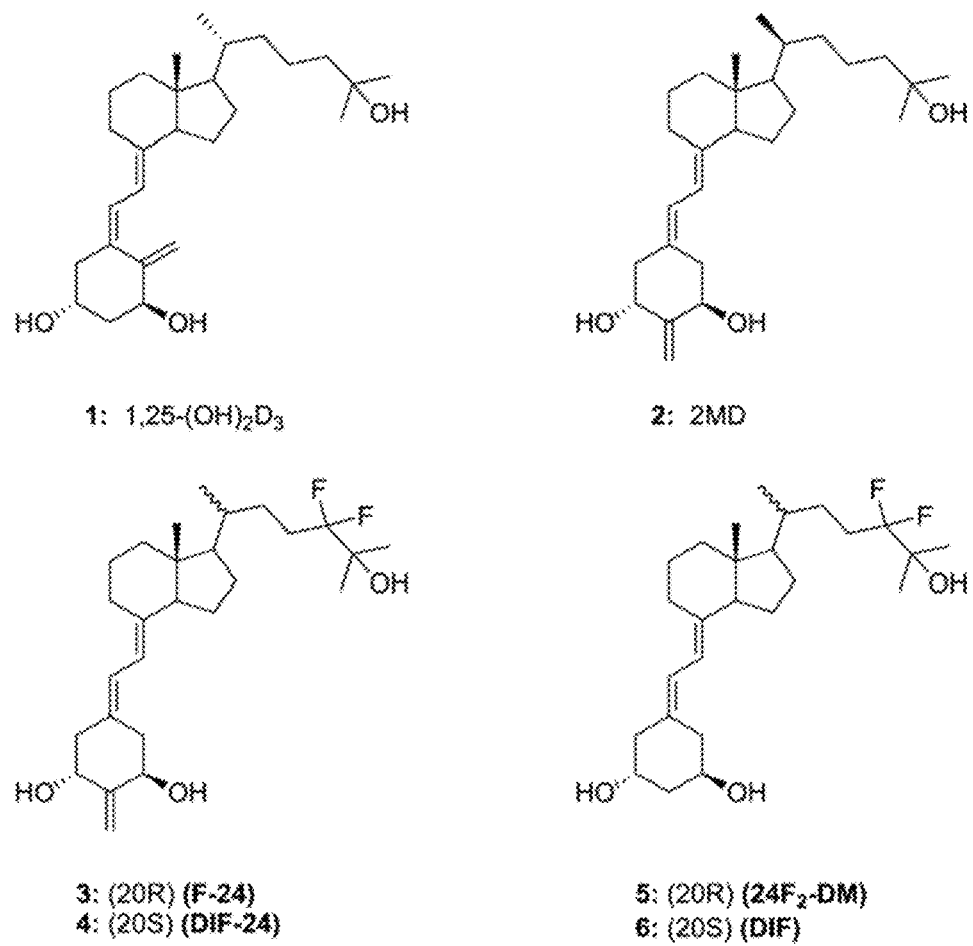
FIG. 1. Structures of the 1α,25-(OH)$_2$D$_3$ (1), 2MD (2) and vitamin D analogues (3-6).
Figure 3:
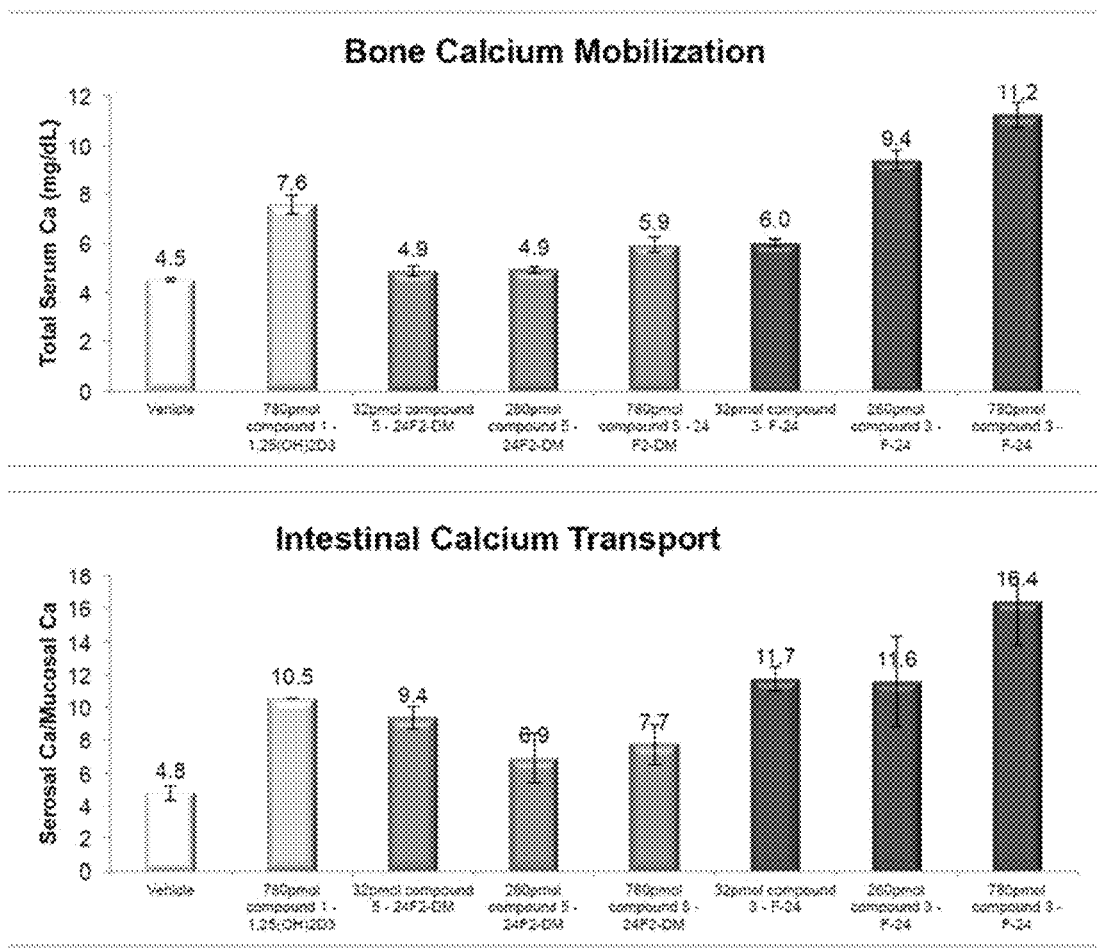
FIG. 3. Total serum calcium levels reflecting the ability of each analog to release bone calcium stores for analogues 3 (F-24) and 5 (24F2-DM). Note: the values shown are the difference from the vehicle controls. In vivo intestinal calcium transport compared to the native hormone for analogues 3 (F-24) and 5 (24F2-DM). Note: the values shown are the difference from the vehicle controls.
Figure 4:
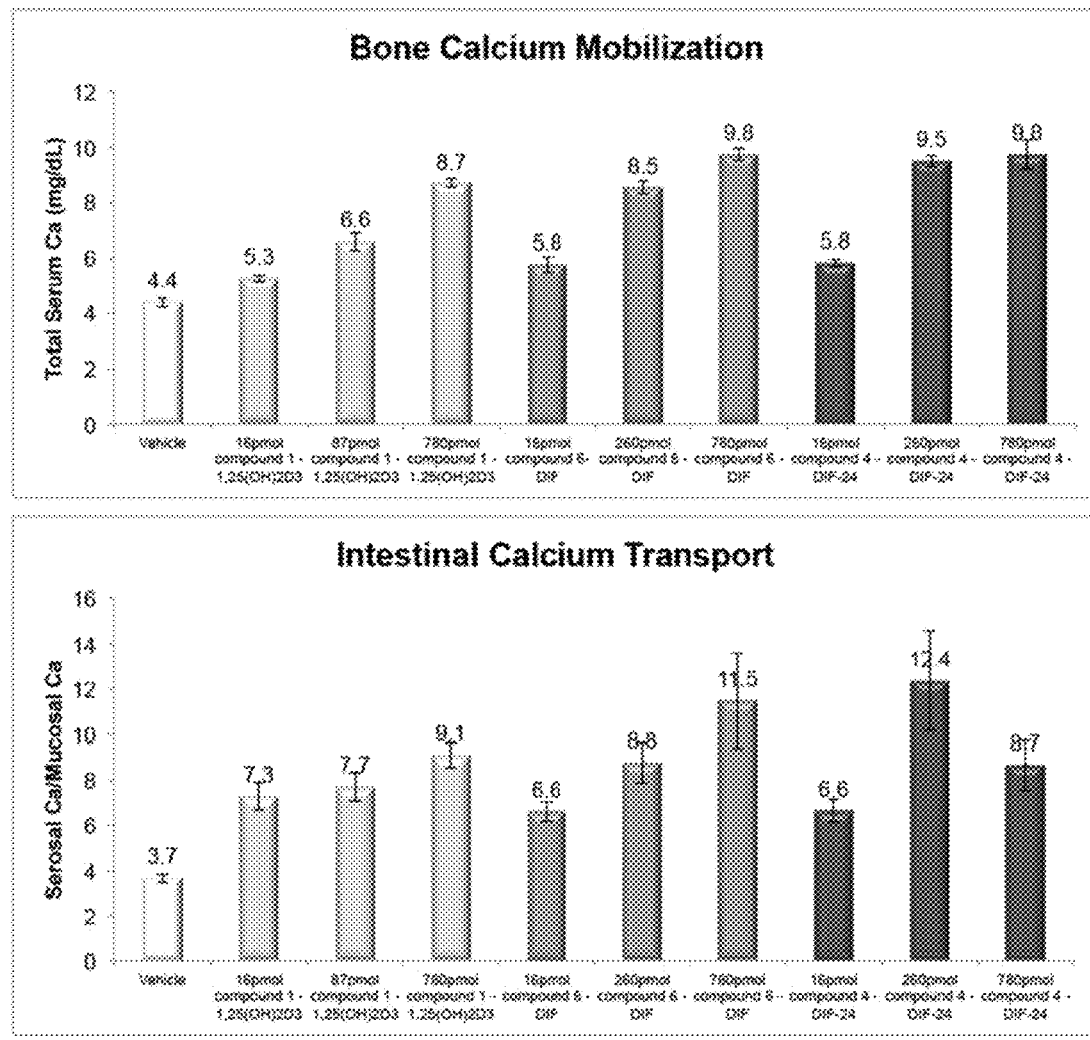
FIG. 4. Total serum calcium levels reflecting the ability of each analogue to release bone calcium stores for analogues for analogues 4 (DIF-24) and 6 (DIF). Note: the values shown are the difference from the vehicle controls. In vivo intestinal calcium transport compared to the native hormone for analogues 4 (DIF-24) and 6 (DIF). Note: the values shown are the difference from the vehicle controls.

The disclosed subject matter further may be described utilizing terms as defined below.

Unless otherwise specified or indicated by context, the terms "a", "an", and "the" mean "one or more." For example, the phrases "a compound" and "an analog" should be interpreted to mean "one or more compounds" and "one or more analogs," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The transitional term "comprising" should be interpreted as being "open-ended" such that a claim utilizing the term "comprising" should be interpreted as requiring the recited components but being permitted to include other additional components. The transitional term "consisting essentially of" should be interpreted as being "partially closed" such that a claim utilizing the term "consisting essentially of" should be interpreted as requiring the recited components and permitting only other additional components that do not materially affect the basic and novel characteristics of the claimed subject matter. The transitional term "consisting" should be interpreted as being "closed" such that a claim utilizing the term "consisting" should be interpreted as requiring the recited components and permitting no other additional components.

As used herein, the terms "1α,25(OH)$_2$D$_3$," "the native hormone," and "calcitriol" may be used interchangeably.

As used herein, the compound "F-24" refers to (20R)-1α, 25-Dihydroxy-24,24-difluoro-2-methylene-19-norvitamin $D_3$.

As used herein, the compound "DIF-24" refers to (20S)-1α,25-Dihydroxy-24,24-difluoro-2-methylene-19-norvitamin $D_3$.

As used herein, the compound "24F$_2$-DM" refers to the compound (20R)-1α,25-Dihydroxy-24,24-difluoro-19-norvitamin $D_3$.

As used herein, the compound "DIF" refers to (20S)-1α, 25-Dihydroxy-24,24-difluoro-19-norvitamin $D_3$.

As used herein, the compound "2MD" refers to 2-methylene-(20S)-1α,25-dihydroxy-19-nor vitamin $D_3$. (See DeLuca et al., U.S. Pat. No. 5,843,928, the contents of which are incorporated herein by reference in its entirety).

The presently disclosed analogs are characterized by the general formula I previously illustrated herein. The pro-drug form and protected-hydroxy form of the presently disclosed analogs also are characterized by general formula I. As contemplated herein, a "protected-hydroxy" group is a hydroxy group derivatized or protected by any of the groups commonly used for the temporary or permanent protection of hydroxy functions (e.g., alkoxycarbonyl, acyl, silyl, or alkoxyalkyl groups). A "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO—groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. As contemplated herein, the word "alkyl" as used in the description or the claims, denotes a straight-chain or branched alkyl radical of 1 to 10 carbons, in all its isomeric forms. "Alkoxy" refers to any alkyl radical which is attached by oxygen (i.e., a group represented by "alkyl-O—"). Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. The terms "hydroxyalkyl", "deuteroalkyl" and "fluoroalkyl" refer to an alkyl radical substituted by one or more hydroxy, deuterium, or fluoro groups respectively. An "alkylidene" refers to a radical having the general formula $C_kH_{2k}$—where K is an integer.

The compounds disclosed herein may be utilized to treat and/or prevent diseases or disorders in patients in need thereof. The terms "patient," "subject," and "individual" may be used interchangeably herein.

A patient in need thereof may include any animal. The animal may be a human, a domestic animal such as a dog or a cat, or an agricultural animal, including fowl like chickens, turkeys, pheasant or quail, as well as equine, bovine, ovine, caprine, or porcine animals.

A patient in need thereof may refer to patient having or at risk for acquiring a disease or disorders associated with vitamin D activity. For example, a patient in need thereof may include a patient having or at risk for acquiring bone diseases and disorders that are associated with vitamin D activity, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. A patient in need thereof may also include a patient in need of an increase in bone strength.

A patient in need thereof may include a patient having or at risk for developing skin diseases, disorders, and conditions (e.g., skin diseases, disorders, and conditions that are associated with vitamin D activity). These may include, but are not limited to psoriasis, acne, lack of adequate skin firmness, lack of adequate dermal hydration, and insufficient sebum secretion.

A patient in need thereof may include a patient having or at risk for developing cell proliferative diseases or disorders such as cancer (e.g., cell proliferative diseases or disorders such as cancer that are associated with vitamin D activity). These may include, but are not limited to leukemia, colon cancer, breast cancer, skin cancer, and prostate cancer.

A patient in need thereof may include a patient having or at risk for developing autoimmune diseases and disorders (e.g., autoimmune diseases and disorders that are associated with vitamin D activity). These may include, but are not limited to multiple sclerosis, diabetes mellitus, lupus, host versus graft reaction, and rejection of transplants.

A patient in need thereof may include a patient having or at risk for developing inflammatory diseases or disorders (e.g., inflammatory diseases or disorders that are associated with vitamin D activity). These may include, but are not limited to rheumatoid arthritis, asthmas, and inflammatory bowel diseases. A patient in need thereof may include having or at risk for developing Crohn's disease and ulcerative colitis.

A patient in need thereof may include a patient having or at risk for developing obesity (e.g., obesity that is associated with vitamin D activity). A patient in need thereof may include a patient in need of or desirous of inhibiting adipocyte differentiation, inhibiting SCD-1 gene transcription, and/or reducing body fat.

A patient in need thereof may include a patient having or at risk for developing secondary hyperparathyroidism (e.g., secondary hyperparathyroidism that is associated with vitamin D activity). In particular, a patient in need thereof may include a patient having or at risk for developing secondary hyperparathyroidism of renal osteodystrophy.

For prevention and/or treatment purposes, the compounds disclosed herein may be formulated as pharmaceutical applications, for example, as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds disclosed herein may be administered by any suitable route of administration including, but not limited to, orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications.

Compositions for use in the disclosed treatment and prevention methods comprise an effective dose of a disclosed compound as an active ingredient and a suitable carrier. An effective dose of such compound for use in accordance with the disclosed methods is high enough for achieving a desired therapeutic effect and low enough so as not as to cause an undesired side effect (e.g., hypercalcemia). In some embodiments, pharmaceutical composition may comprise the disclosed compounds in a minimal dose of at least about 0.01, 0.05, 0.1, 0.5, 1.0, 5.0, 10.0, 50.0, 100.0, 500.0 or 1000.0 µg/gm of the composition. In other embodiments, pharmaceutical composition may comprise the disclosed compounds in a maximal dose no greater than 1000.0, 500.0, 100.0, 50.0, 10.0, 5.0, 1.0, 0.1, 0.05 µg/gm of the composition. In other embodiments, pharmaceutical compositions may comprise the disclosed compounds within dose ranges having as end-points any of these disclosed doses (e.g., 0.01-1000.0 µg/gm of the composition). Minimal and/or maximal doses may be administered at any suitable frequency, such as daily, three times per week, weekly, or other frequencies.

In the disclosed treatment and prevention methods, a patient in need thereof may be administered an effective dose level of a disclosed compound. An effective dose level of such compound for use in accordance with the disclosed methods is high enough for achieving a desired therapeutic effect and low enough so as not as to cause an undesired side effect (e.g., hypercalcemia). In some embodiments, a minimal dose level for achieving therapy may be at least about 0.1, 0.25, 0.5, 1.0, 2.5, 5.0, 10.0, 12.5, 15.0, or 20.0 ng/kg body weight of the subject. In some embodiments, a maximal dose level may not exceed about 20.0, 15.0, 12.5, 10.0, 5.0, 2.5, 1.0, 0.5, 0.25, and 0.1 ng/kg body weight of the subject. In other embodiments, minimal and/or maximal dose levels may include dose level ranges having as end-points any of these disclosed dose levels (e.g., 0.1-20.0 ng/kg body weight of the subject). Minimal and/or maximal dose levels may be administered at any suitable frequency, such as daily, three times per week, weekly, or other frequencies.

The disclosed compounds may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The disclosed compounds may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

Experimental Methods

Title: A Methylene Group on C-2 of 24,24-Difluoro-19-nor-1,25-Dihydroxyvitamin $D_3$ Markedly Increases Bone Calcium Mobilization In Vivo Reference is made to the manuscript entitled "A Methylene Group on C-2 of 24,24-Difluoro-19-nor-1,25-Dihydroxyvitamin $D_3$ Markedly Increases Bone Calcium Mobilization in vivo," authored by Agnieszka Flores, Ilaria Massarelli, James B. Thoden, Lori A. Plum, and Hector F. DeLuca, and published in the Journal of Medicinal Chemistry, 2015 Dec. 24; 58(24):9731-41; doi: 10.1021/acs.jmedchem.5b01564; Epub 2015 Dec. 9, the content of which manuscript is incorporated in this application by reference in its entirety.

Abstract

Four side chain fluorinated analogues of 1α,25-dihydroxy-19-norvitamin (1) have been prepared in convergent syntheses using the Wittig-Horner reaction as a key step. Structures and absolute configurations of analogues 3 and 5 were confirmed by X-ray crystallography. All analogues showed high potency in HL-60 cell differentiation and vitamin D-24-hydroxylase (24-OHase) transcription as compared to 1α,25-dihydroxyvitamin $D_3$ (1). Most important is that all of the 20S-configured derivatives had high bone mobilizing activity in vivo. However, in the 20R series, a 2-methylene group was required for high bone mobilizing activity. A change in positioning of the 20R molecule in the vitamin D receptor when the 2-methylene group is present may provide new insight into the molecular basis of bone calcium mobilization induced by vitamin D.

Introduction

The biologically active metabolite of vitamin $D_3$ [calcitriol, 1α,25-(OH)$_2$D$_3$ (1); FIG. 1] is best known for its regulation of calcium and phosphorus homeostasis, but it also plays a role in controlling other biological functions such as induction of cell differentiation or proliferation. The use of calcitriol in hyperproliferative disorders is limited by its calcemic effects, hence the continuous interest in chemically modified analogues of 1α,25-(OH)$_2$D$_3$ and their clinical applications.[1]

The hormone (1) undergoes chemical transformations in vivo, such as 23S- and 24R-hydroxylation catalyzed by CYP24A1 hydroxylase, oxidation of the 24-hydroxy group to a ketone, and cleavage of the C-23-C-24 bond of (23S)-23,25-dihydroxy-24-oxovitamin D$_3$.[2] Preventing or slowing this catabolic degradation, for instance introducing fluorine atoms, results in analogues with a longer life-time, more resistant to oxidation.[3] The substitution of the hydrogen atoms with fluorine is dictated by physical and chemical properties. The high electronegativity of fluorine, its small size, the good overlap of the 2s or 2p orbitals with corresponding orbitals of carbon as well as the presence of three lone pairs of electrons mean that bonds are always polarized from the sp$^3$ carbon (δ$^+$) to the fluorine (δ$^-$). Because of the C—F bond stability and a similar size of the hydrogen and fluorine atoms, fluorinated vitamin D analogues have been applied as catabolism inhibitors.[4,5]

First, fluorine-substituted side-chain analogues were synthesized in the early 1980s. The use of 24,24-difluoro-25-hydroxyvitamin D$_3$ was used to show that 24-hydroxylation is not required for the action of vitamin D.[6] Falecalcitriol (26,27-hexafluorocalcitriol) marketed for the treatment of hypocalcemia, rickets, and osteomalacia was found several times more potent then calcitriol in both in vitro and in vivo systems, with a longer duration of its action in vivo.[7] Numerous other modifications on the fluorinated side chain (e.g., a double[8-10] and a triple[9] bonds, sulfone,[8] a carbonyl group,[10] oxetan[11]) as well as introduction of a fluorine atom on the A ring of vitamin D$_3$ have also been investigated.[12]

It has been found that 20-epimerization of 1α,25-(OH)$_2$D$_3$ increases biological activity, while the combination of C-20 epimerization and the shift of the methylene group from C-10 to C-2 greatly increase both bone synthesis and resorption. We have now found that a C-20-methylene substitution markedly increases bone calcium mobilizing activity only when the configuration of C-20 is R in 24,24-difluoro-19-nor-1α,25-dihydroxyvitamin D compounds. When the C-20 is S, 2-methylene substitution has no impact on bone calcium mobilization activity.

Results

Synthesis. Takayama et al. synthesized 24,24-difluoro-1α,25-(OH)$_2$D$_3$ starting from commercially available lithocholic acid and using (diethylamino)sulfur trifluoride (DAST) as a fluorinating reagent.[5,13] The same group proposed an alternative route that involved as a starting compound 1α,3β-bis[tert-butyldimethylsilyl)oxy]androst-5-ene to obtain 24,24-difluoro-1α,25-(OH)$_2$D$_3$ in 4% total yield through 10 steps.[14]

Since organofluorine compounds are often hazardous and corrosive substances (e.g., elemental fluorine, hydrofluoric acid) the syntheses of fluorinated molecules often use building blocks and synthons already containing fluorine. As shown in Scheme 1, the vitamin D analogues 3 and 5 were prepared from the 20R- and 20S-nitriles 7 and 8.[15] The reduction of the obtained nitriles with DIBALH afforded the respective aldehydes 9[16] and 10 in 90% and 99% yield. The Reformatsky reagent, prepared from ethyl bromodifluoroacetate, adds onto aldehydes and imines. This difluoromethylation method has been widely applied in medicinal chemistry.[17] Posner et al. synthesized 24-difluorinated hybrid analogues of 1α,25-(OH)$_2$D$_3$ in a Reformatsky reaction using ethyl bromodifluoroacetate and activated zinc to obtain gem-difluoro ester alcohols as a 1:1 ratio of diastereomers.[18] A useful alternative to Zn-promoted Reformatsky reactions are lanthanide reagents.[19] We have used samarium (II) iodide for the initiation of a radical reaction of bromodifluoroacetate with aldehydes 9 and 10 in Barbier conditions to prepare α,α-difluoro-β-hydroxyesters 11a,b and 12a,b in 45% and 66% yield, respectively. Deoxygenation of alcohols 11a,b and 12a,b was performed in the Barton-McCombie[20] reduction in the two consecutive reactions, first with 1,1'-thiocarbonyldiimidazole to give thionocarbonates 13a,b and 12a,b, then with triethylsilane and benzoyl peroxide that afforded esters 15 and 16 in 82% and 65% yield (over 2 steps). The esters 15 and 16 were treated with methylmagnesium bromide, and then with tetrabutylammonium fluoride to remove silyl protecting groups to obtain diols 19 and 20 in 90% and 95% yield. The compounds 19 and 20 were subsequently oxidized with tetrapropylammonium perruthenate in the presence of 4-methylmorpholine N-oxide and, in the formed product the 25-hydroxy group was protected as a TES ether to give the Grundmann ketones 21 and 22 in 45% and 82% overall yield. In contrast to syntheses starting from steroids, we used a convergent approach based on the phosphine oxide coupling to prepare the vitamin D$_3$ analogues 3-6 (Scheme 1).

Scheme 1.

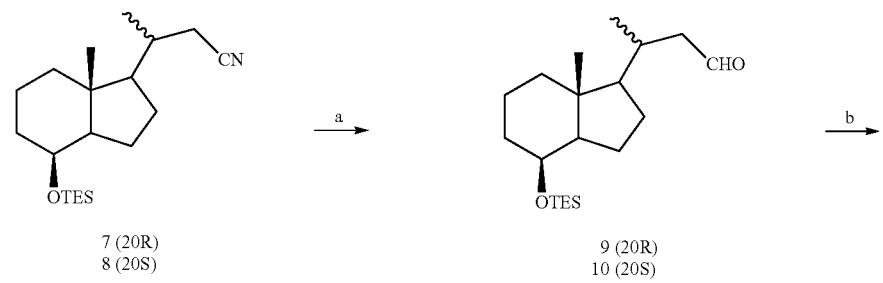

7 (20R)
8 (20S)

9 (20R)
10 (20S)

-continued

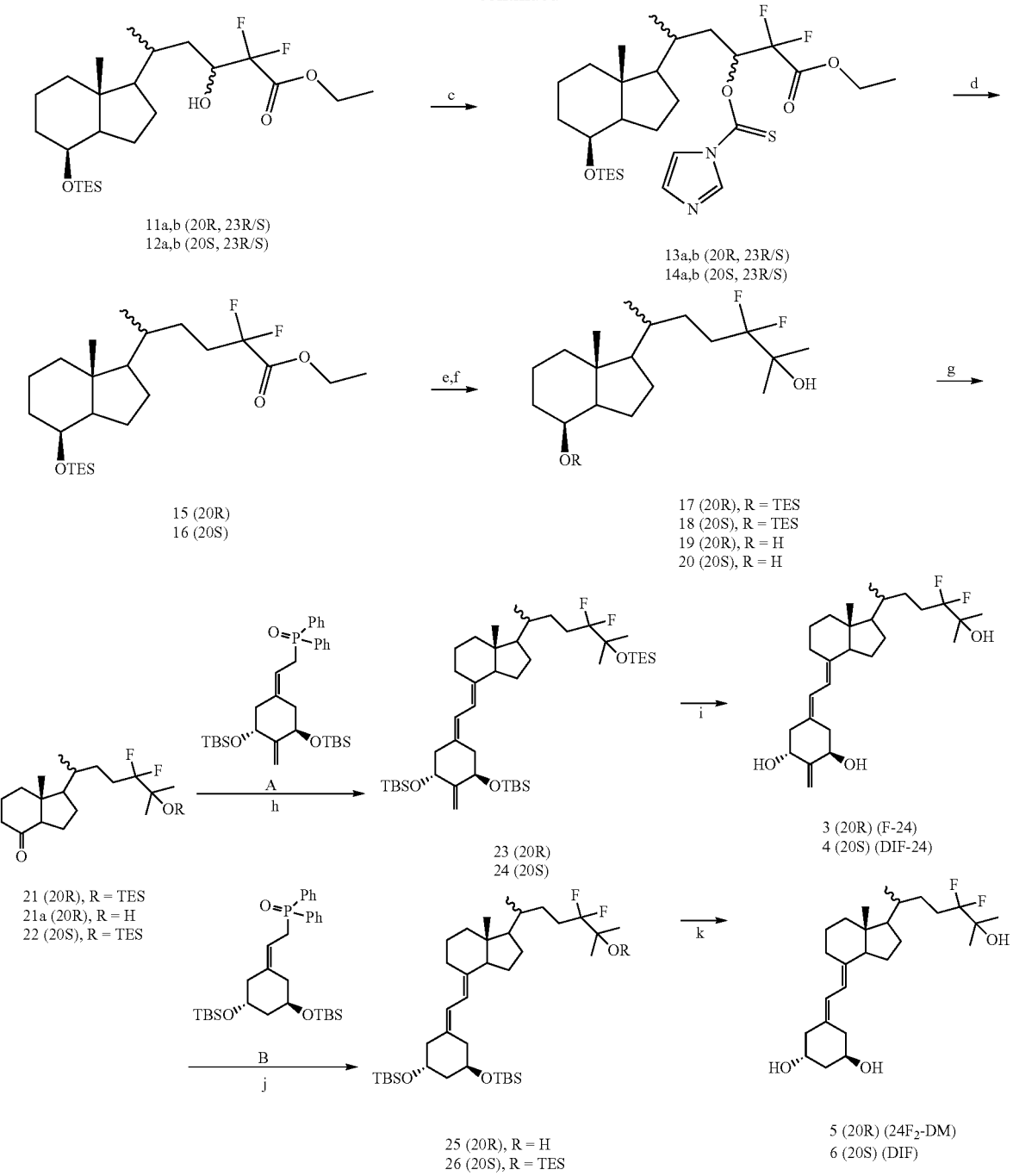

(a) DIBAL, CH$_2$Cl$_2$; (b) BrCF$_2$CO$_2$Et, SmI$_2$, THF; (c) 1,1'-Thiocarbonyldiimidazole, THF; (d) Et$_3$SiH, [PhC(O)]$_2$O$_2$, toluene; (e) CH$_3$MgBr, Et$_2$O; (f) TBAF, THF; (g) (1) NMO, TPAP, 4Å mol. sieves, CHCl$_2$; (2) TESOTf, 2,6-lutidine, CH$_2$Cl$_2$; (h) PhLi, THF; (i) 48% aq. HF, MeCN, THF; (j) PhLi, THF; (k) 48% aq. HF, MeCN, THF.

In this method, first developed by Lythgoe et al.[21] an anion of an allylic phosphine oxide reacts with the Grundmann ketone via the Wittig-Horner reaction. The known phosphine oxide A[22] was treated with phenyllithium to generate the anion, coupled with the ketones 21 and 22 to give the corresponding protected 19-norvitamin D analogues 23 and 24 in 61% and 59% yield. The silyl protecting groups were removed with hydrofluoric acid to give the final compounds 3 and 4 in 72% and 79% yield, respectively. The structure and absolute configuration of the vitamin 3 was confirmed by X-ray crystallography (FIG. 2). The anion generated from the phosphine oxide B[24] was subjected to the Wittig-Horner coupling with both ketones 21a and 22 to give vitamin D$_3$ analogues 25 and 26 in 29% and 58% yield. After removal of the silyl groups in the products 25 and 26 the corresponding vitamin D$_3$ analogues 5 and 6 were obtained in 59% and 23% yield, respectively. The structure and absolute configurations of compound 5 was confirmed by X-ray crystallography (FIG. 2).

Biological Evaluation. Biological activities in vitro of the 24,24-$F_2$ analogues described above are summarized in Table 1. All 24-fluoro compounds bound to the vitamin D receptor with high affinity almost equal to that of 1α,25-$(OH)_2D_3$[22], while the 20S-2-methylene analogue 5 was slightly more effective than 1α,25-$(OH)_2D_3$. All analogues were superior to 1α,25-$(OH)_2D_3$ in causing the differentiation of HL-60 cells with analogue 2, the 2-methylene-20S compound being more active than 1α,25-$(OH)_2D_3$. This pattern was repeated in the CYP24A1 transcription test.

TABLE 1

VDR Binding Properties,[a] HL-60 Differentiating Activities,[b] and Transcriptional Activities[c] of the Vitamin D Hormone (1), 2MD (2) and the vitamin D Analogues 3-6.

| Comp. No. | Side-chain structure | VDR binding $K_i$ (nM) | ratio | HL-60 differentiation $ED_{50}$ (nM) | ratio | 24OHase transcription $ED_{50}$ (nM) | Ratio |
|---|---|---|---|---|---|---|---|
| 1 (1α,25-$(OH)_2D_3$) | | 0.04 | 1 | 3 | 1 | 0.2 | 1 |
| 2 (2MD) | | 0.03 | 1.3 | 0.02 | 150 | 0.007 | 29 |
| 3 (F-24) | | 0.04 | 1 | 0.1 | 30 | 0.01 | 20 |

TABLE 1-continued

VDR Binding Properties,[a] HL-60 Differentiating Activities,[b] and Transcriptional Activities[c] of the Vitamin D Hormone (1), 2MD (2) and the vitamin D Analogues 3-6.

| Comp. No. | Side-chain structure | VDR binding $K_i$ (nM) | ratio | HL-60 differentiation $ED_{50}$ (nM) | ratio | 24OHase transcription $ED_{50}$ (nM) | Ratio |
|---|---|---|---|---|---|---|---|
| 4 (DIF-24) | | 0.03 | 1.3 | 0.03 | 100 | 0.02 | 10 |
| 5 (24F$_2$-DM) | | 0.02 | 2 | 0.05 | 60 | 0.04 | 5 |
| 6 (DIF) | | 0.03 | 1.3 | 0.06 | 50 | 0.04 | 5 |

[a]Competitive binding of 1□,25-(OH)$_2$D$_3$ (1) and the synthesized vitamin D analogues to the full-length recombinant rat vitamin D receptor. The experiments were carried out in duplicate on two different occasions. The $K_i$ values are derived from the dose-response curves and represent the inhibition constant when radiolabeled 1□,25-(OH)$_2$D$_3$ is present at 1 nM and a $K_d$ of 0.2 nM is used. The binding ratio is the average ratio of the 1□,25-(OH)$_2$D$_3$ $K_i$ to the $K_i$ for the analogue. [b]Induction of differentiation of HL-60 promyelocytes to monocytes by 1□,25-(OH)$_2$D$_3$ (1) and the synthesized vitamin D analogues. Differentiation state was determined by measuring the percentage of cells reducing nitro blue tetrazolium (NBT). The experiment was repeated in duplicate two times. The $ED_{50}$ values are derived from the dose-response curves and represent the analogue concentration capable of inducing 50% maturation. The differentiation activity ratio is the average ratio of the 1□,25-(OH)$_2$D$_3$ $ED_{50}$ to the $ED_{50}$ for the analogue. [c]Transcriptional assay in rat osteosarcoma cells stably transfected with a 24-hydroxylase gene reporter plasmid. The $ED_{50}$ values are derived from dose-response curves and represent the analogue concentration capable of increasing the luciferase activity by 50%. The luciferase activity ratio is the average ratio of the 1□,25-(OH)$_2$D$_3$ $ED_{50}$ to the $ED_{50}$ for the analogue.

The in vivo results differ from the in vitro measurements. Certainly in this series, the 20S configuration supported the highest bone mobilization activity. Thus, compounds 4 and 6 had the highest bone mobilization activity and the presence or absence of the 2-methylene group made little difference in that parameter. When the configuration of the C-20 was R, the 2-methylene group had a strong positive effect on the bone mobilizing activity resulting in activity equaling that of the 20S-2-methylene member of the series, compound 4. Thus, the 20R compound without the 2-methylene had less bone calcium mobilization activity than $1\alpha,25\text{-}(OH)_2D_3$. Exactly why the presence of a 2-methylene group greatly increases bone mobilization activities of the 20R compound remains unknown, but must result from a small change in the position of the ligand in the VDR pocket.

All compounds were active on intestinal calcium transport and since all values were high at the lowest dose (16 pmol), it was not possible to assign superior activity on intestinal calcium transport to any analogue in this series.

These results all show that the 24,24-difluoro substituted 19-nor-20S-2-methylene-$1\alpha,25\text{-}(OH)_2D_3$ is one of the most biologically active vitamin D compounds with bone calcium mobilization activity rivaling 2-methylene-19-nor-(20S)-1, 25-dihydroxyvitamin $D_3$ or 2MD. Furthermore, the 2-methylene substitution allows the 24,24-difluoro-1a-hydroxy-19-nor-vitamin $D_3$ to achieve equally high bone mobilizing activity as its 20S counterpart.

Figure 5:
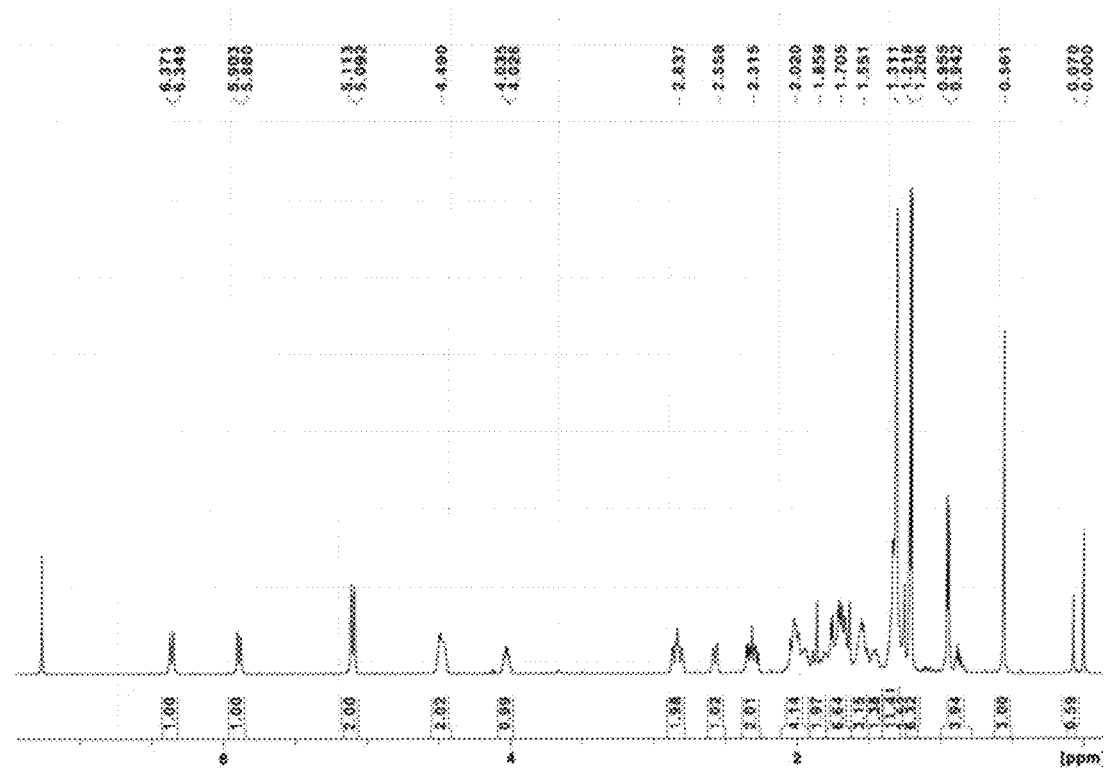
FIG. 5. $^1$H NMR spectrum of the vitamin D analog 3 (F-24).
Figure 6:
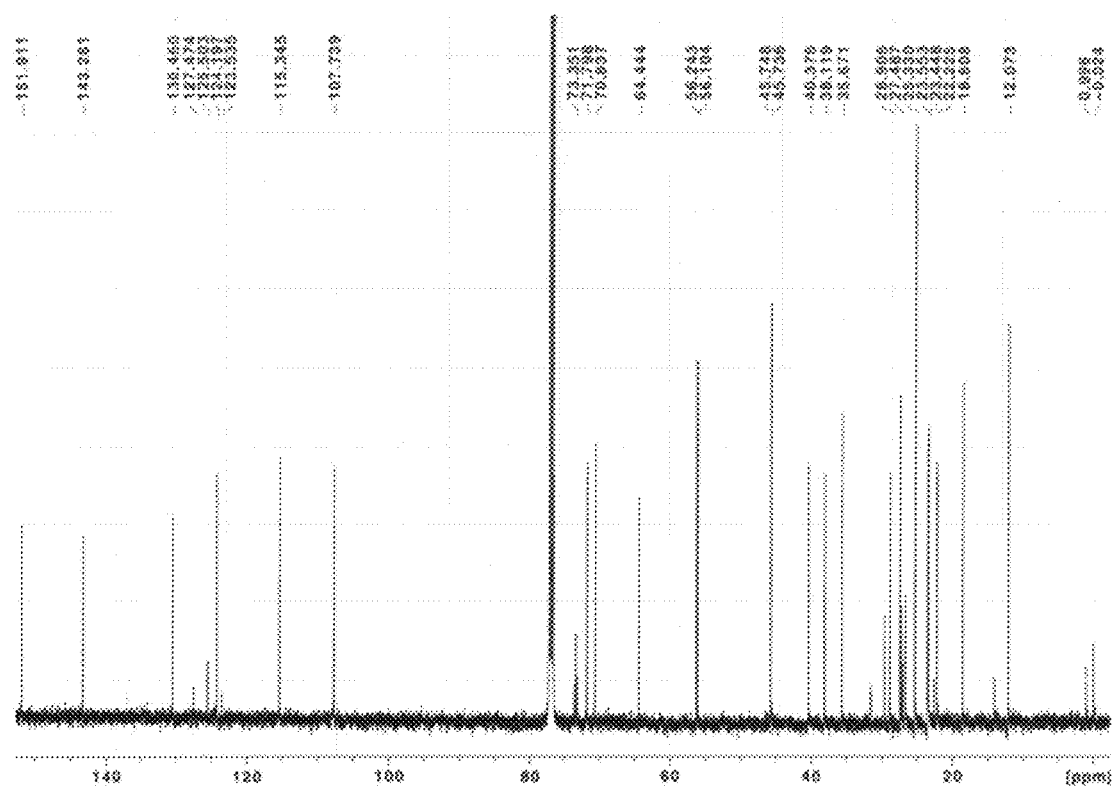
FIG. 6. $^{13}$C NMR spectrum of the vitamin D analog 3 (F-24).
Figure 7:
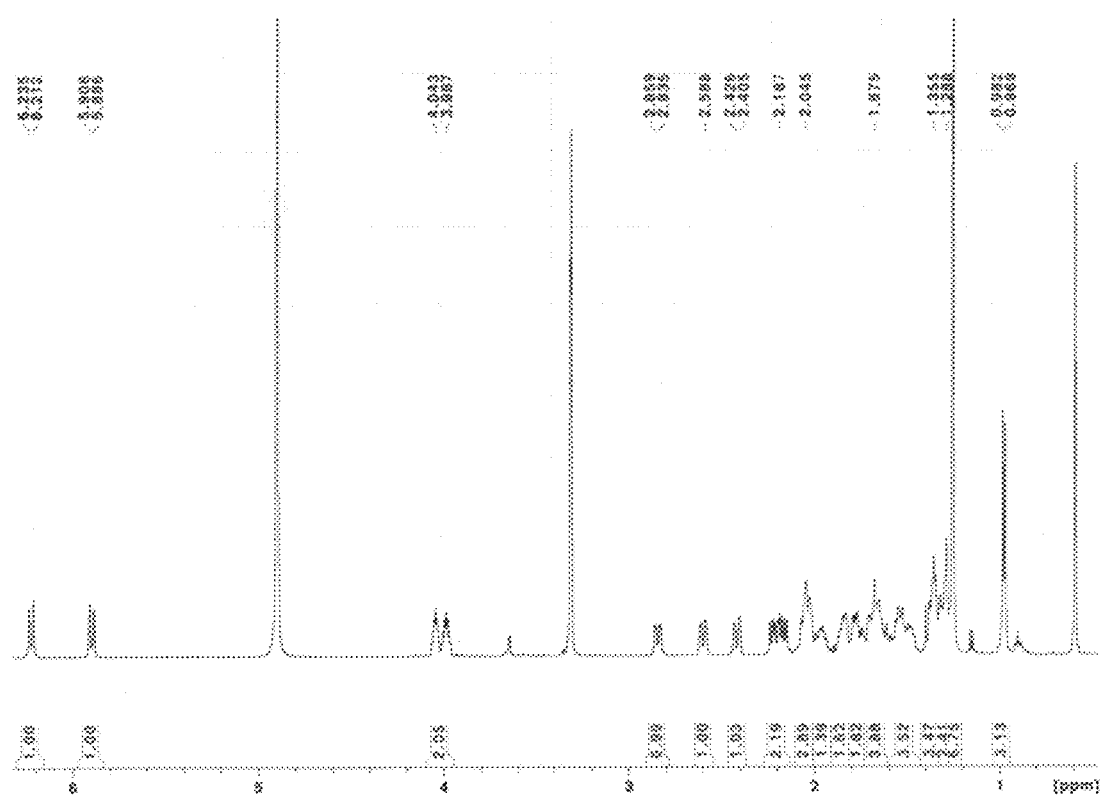
FIG. 7. $^1$H NMR spectrum of the vitamin D analog 4 (DIF-24).
Figure 8:
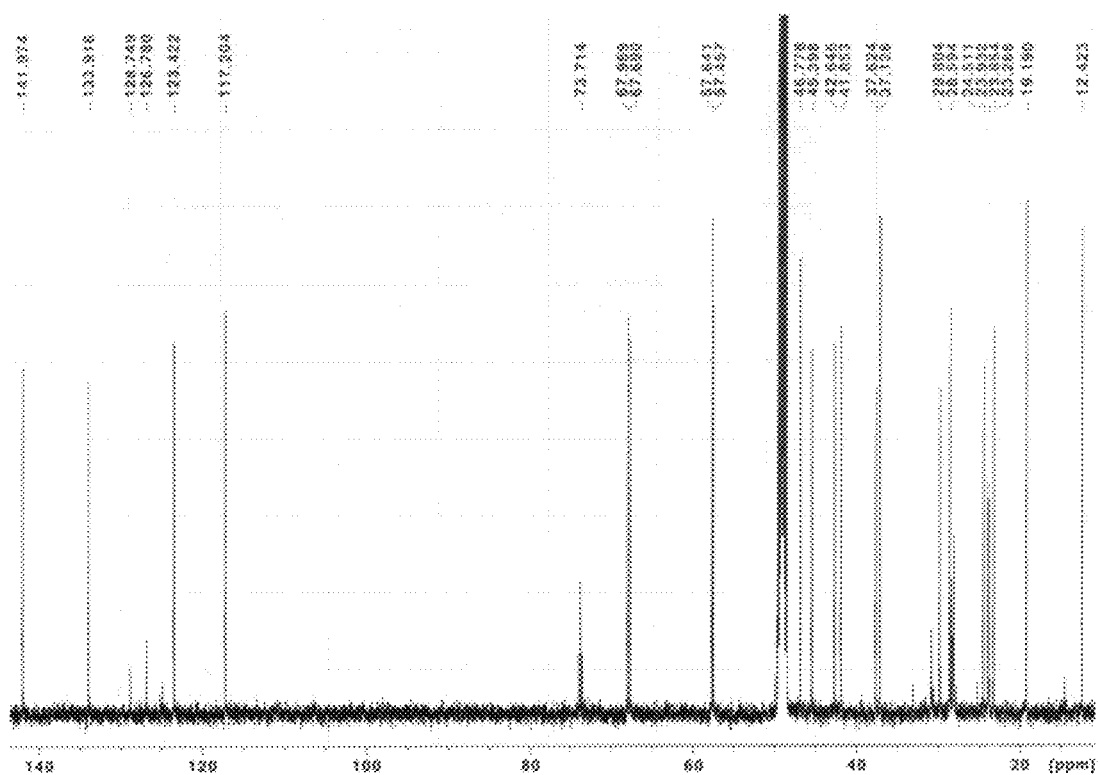
FIG. 8. $^{13}$C NMR spectrum of the vitamin D analog 4 (DIF-24).
Figure 9:
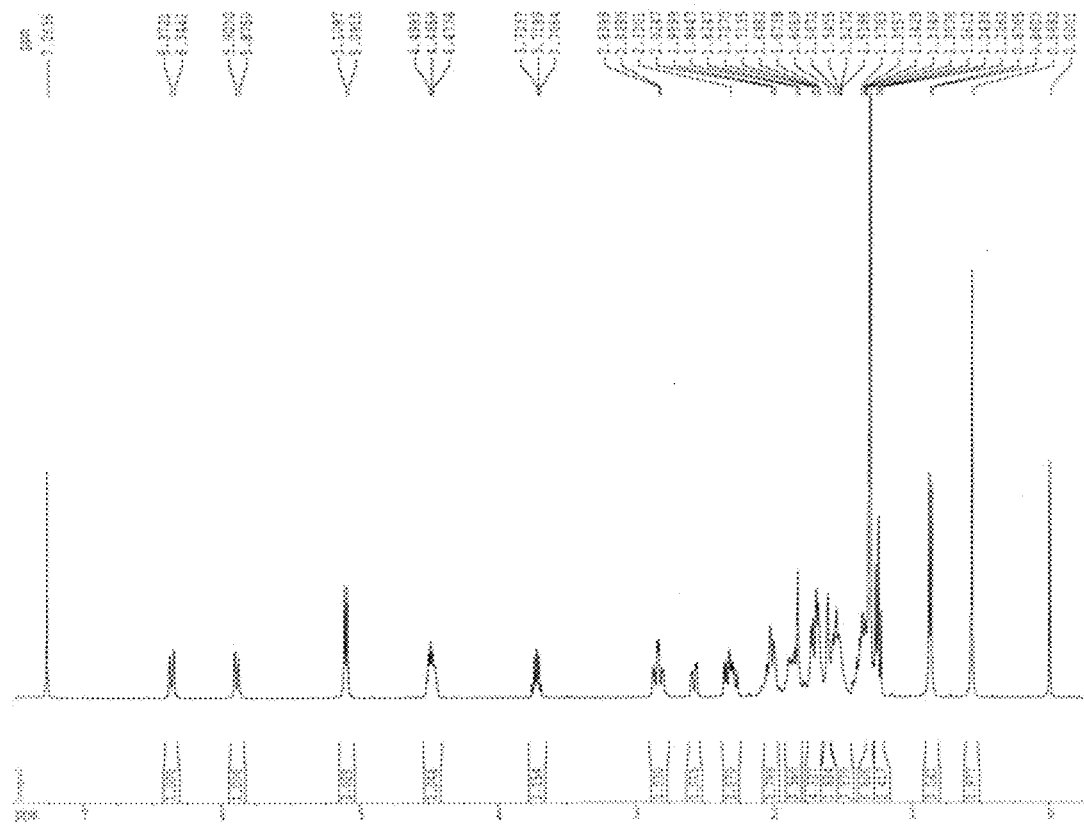
FIG. 9. $^1$H NMR spectrum of the vitamin D analog 5 (24F2-DM).
Figure 10:
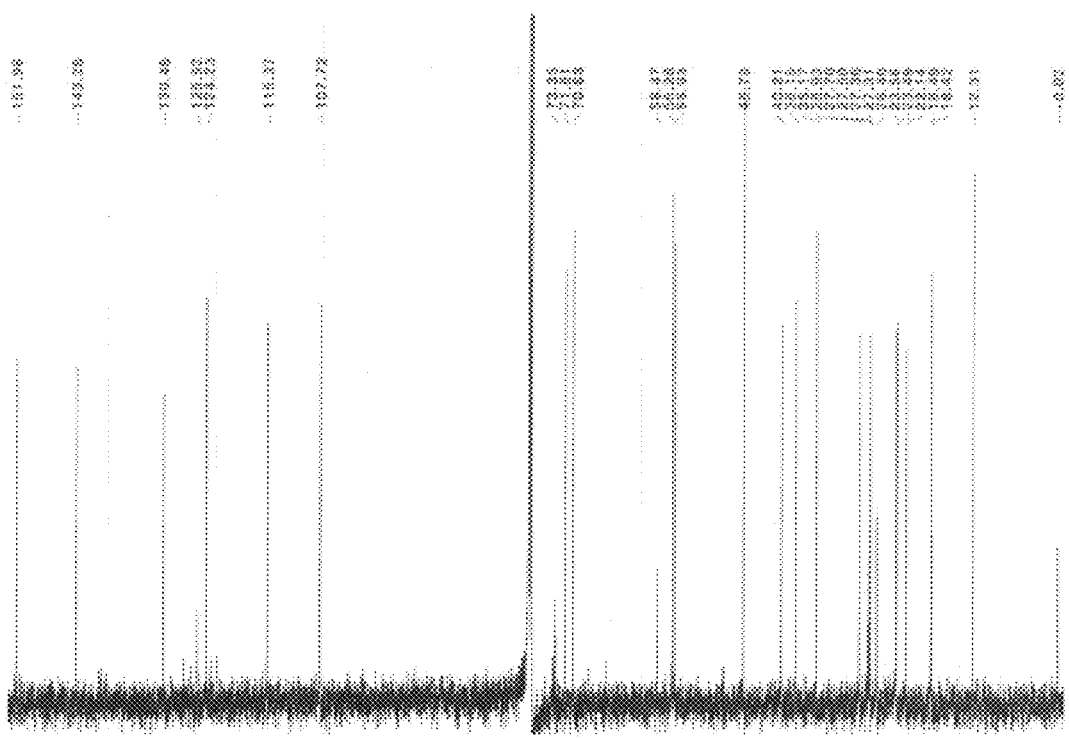
FIG. 10. $^{13}$C NMR spectrum of the vitamin D analog 5 (24F2-DM).
Figure 11:
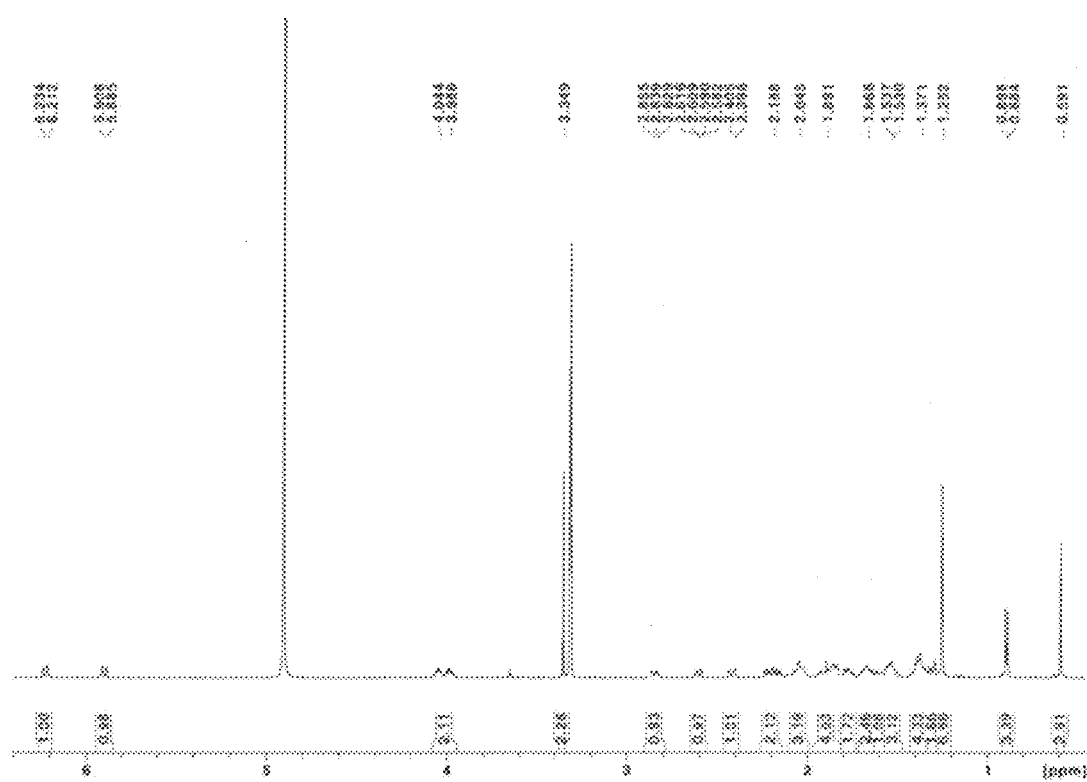
FIG. 11. $^1$H NMR spectrum of the vitamin D analog 6 (DIF).
Figure 12:
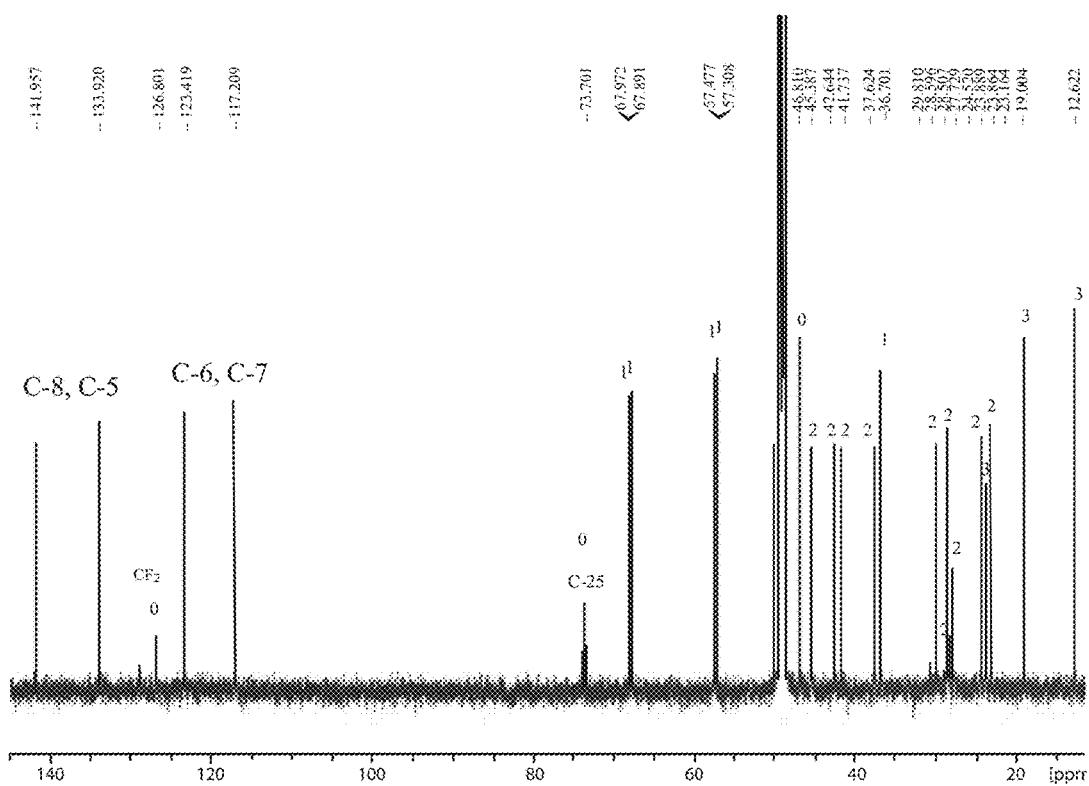
FIG. 12. $^{13}$C NMR spectrum of the vitamin D analog 6 (DIF).
Figure 13:
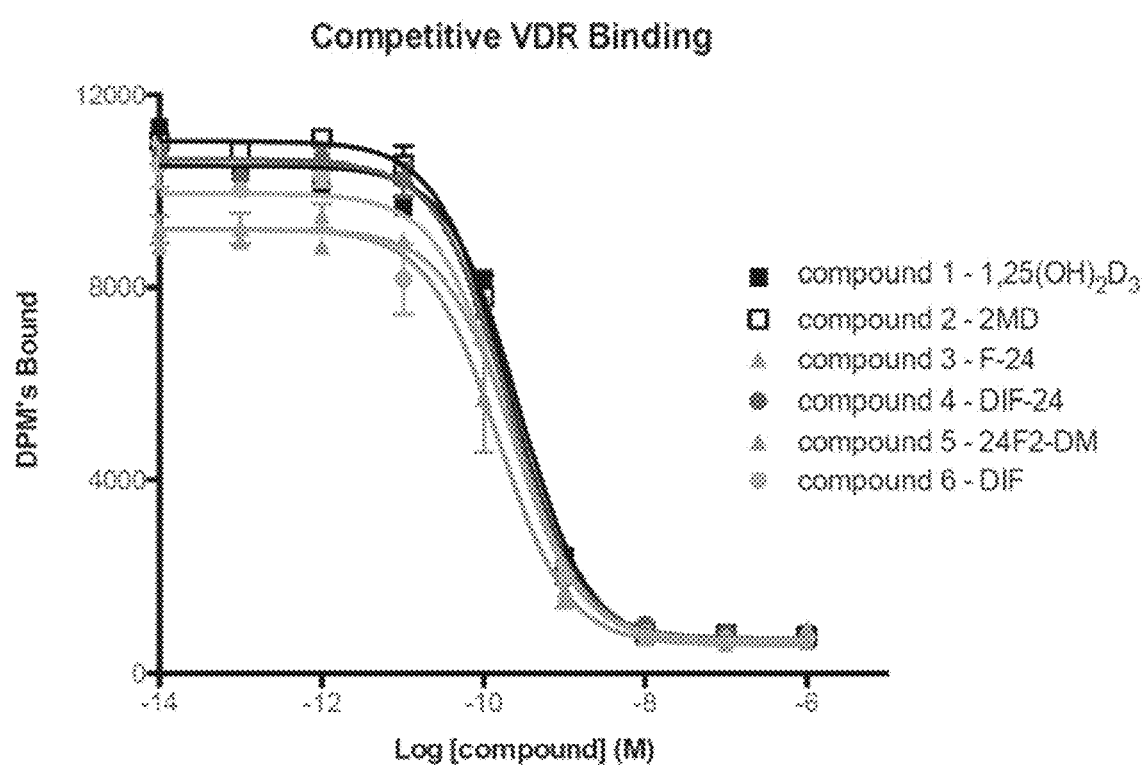
FIG. 13. Competitive VDR binding by 1α,25-(OH)$_2$D$_3$ (1), 2MD (2) and the synthesized vitamin D analogues 3-6.
Figure 14:
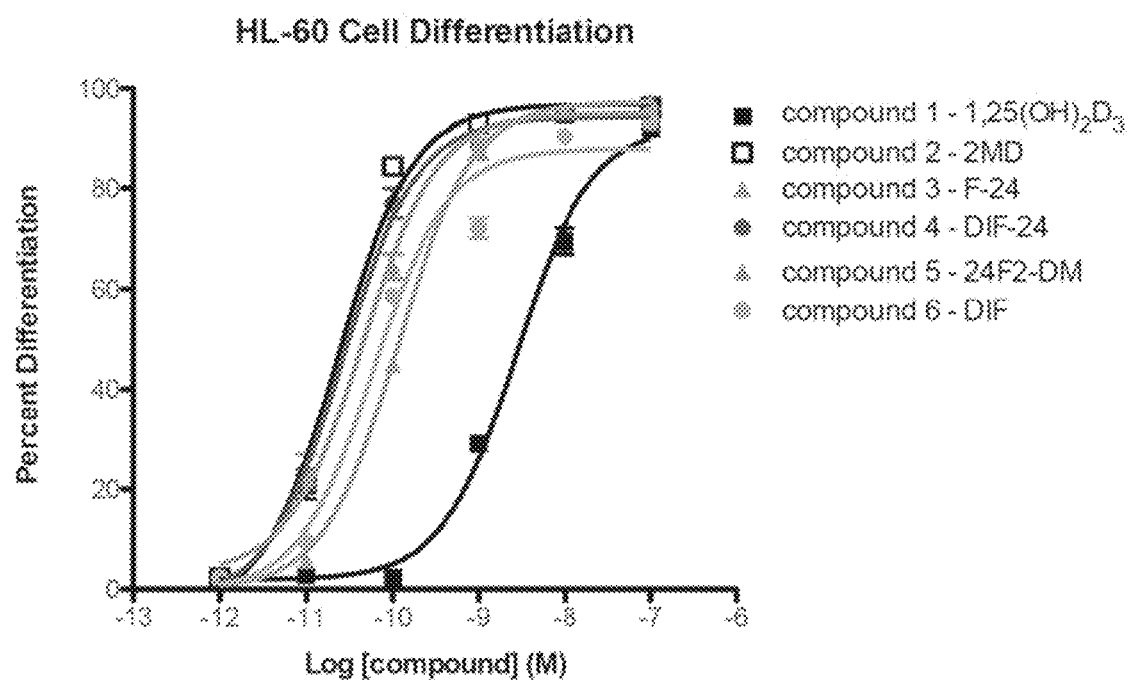
FIG. 14. Induction of differentiation of HL-60 promyelocytes to monocytes by 1α,25-(OH)$_2$D$_3$ (1), 2MD (2) and the synthesized vitamin D analogues 3-6.
Figure 15:
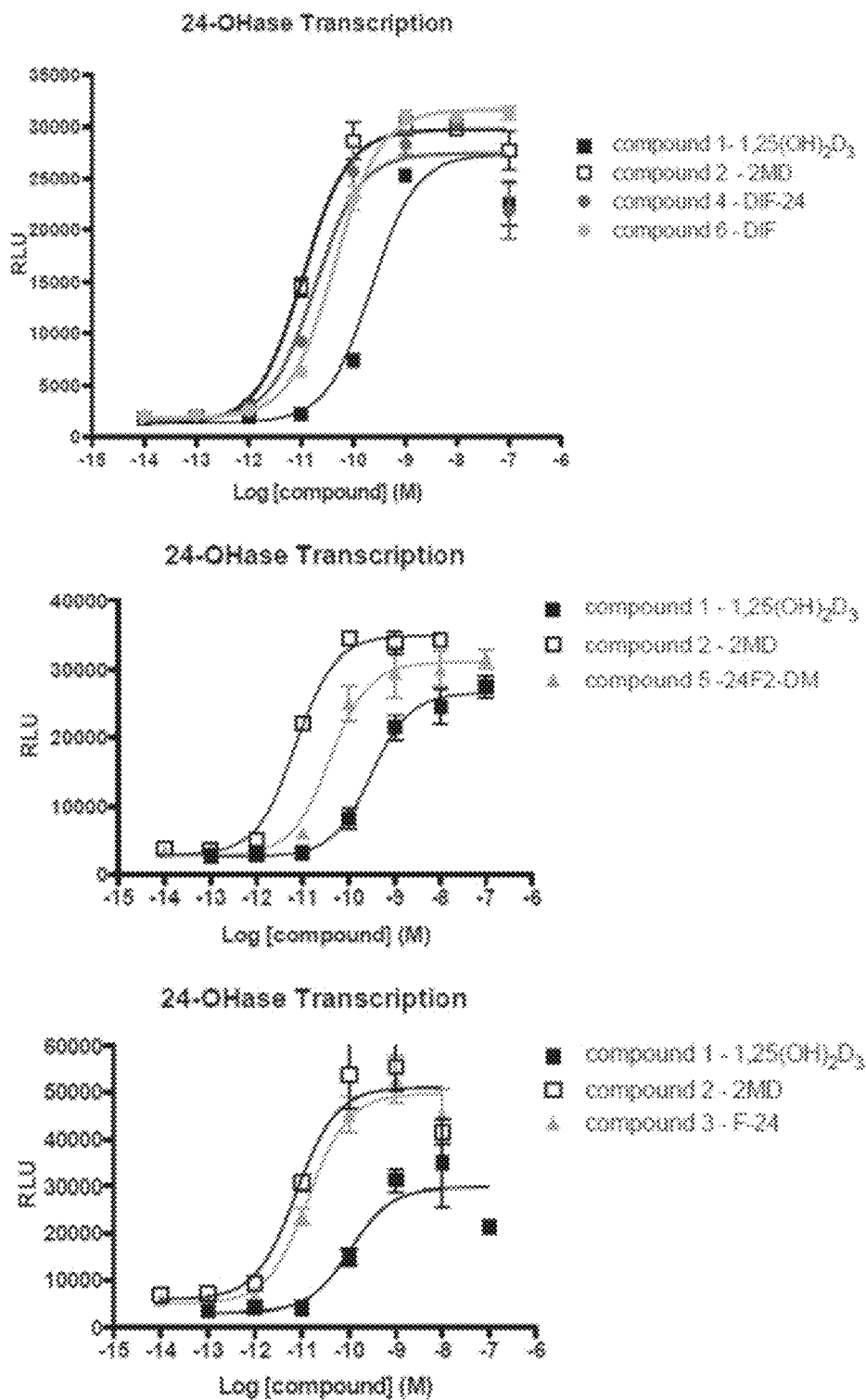
FIG. 15. 24-OHase transcription of 1α,25-(OH)$_2$D$_3$ (1), 2MD (2) and the synthesized vitamin D analogues 3-6.

Discussion. 2-Methylene-19-nor-(20S)-$1\alpha,25$-dihydroxyvitamin $D_3$ (2MD) is a form of vitamin $D_3$ that has greatly increased bone calcium mobilizing activity. Increased in vivo activity in general was expected since 20S-1,25-$(OH)_2D_3$ is more active than its 20R counterpart. However, 2MD is selective in that intestinal calcium absorption is not increased above that found with 1,25-$(OH)_2D_3$. The presence of the 2-methylene group seems to impart selectivity for 20S and less so for the 20R form of 2MD. In this series where the 24-position is blocked with fluoro groups, the 2-methlylene group markedly increases bone mobilization activity only in the 20R compounds, while it makes little or no difference in the 20S compounds (see 3 vs. 5 in FIGS. 5 and 6). This is likely the result of how the 2-methylene group affects positioning of the molecule in the VDR.

All the analogues showed higher transcriptional activities then $1\alpha,25\text{-}(OH)_2D_3$, and analogue 4, structurally the most similar to 2MD, was almost as active as 2MD. Discrepancy between in vitro and in vivo results could be explained by the presence of fluorine atoms affecting metabolism and slowing catabolic degradation of the analogues. Notably, compounds 3 and 5 showed a high potency in HL-60 differentiation but were not as potent in vivo as analogues 4 and 6.

Our results confirm the concept that a 20S configuration markedly increases the bone mobilizing activity of 1α-hydroxylated vitamin D compounds as shown here with the difluoro derivatives. Quite surprisingly, a 2-methylene group markedly increases bone mobilizing activity of the 20R (natural configuration) compounds, but does not impart this activity in the 20S compounds.

Experimental Section

Chemistry. Melting points (uncorrected) were determined on a Thomas-Hoover capillary melting point apparatus. Optical rotations were measured in chloroform using a Perkin-Elmer model 343 polarimeter at 22° C. Ultraviolet (UV) absorption spectra were recorded with a Perkin-Elmer Lambda 3B UV-vis spectrophotometer in ethanol or hexane. $^1$H nuclear magnetic resonance (NMR) spectra were recorded in deuteriochloroform at 400 and 500 MHz with Bruker Instruments DMX-400 and DMX-500 Avance console spectrometers. In the case of diastereomeric mixtures of compounds, proton signals belonging to the major isomer are listed; selected signals of the minor isomer are marked in italic. $^{13}$C NMR spectra were recorded in deuteriochloroform at 100 and 125 MHz with the same Bruker Instruments. Chemical shifts (δ) are reported in parts per million relative to $(CH_3)_4Si$ (δ 0.00) as an internal standard. Abbreviations used are singlet (s), doublet (d), triplet (t), quartet (q), multiplet (m). Numbers in parentheses following the chemical shifts in the $^{13}$C NMR spectra refer to the number of attached hydrogens as revealed by DEPT experiments. $^{19}$F NMR spectra were recorded in deuteriochloroform at 376 MHz with Bruker Instruments. Chemical shifts (δ) are reported in parts per million relative to 1% dichlorodifluoroethane, containing 10% $CCl_3F$ and 6% $(CH_3)_4Si$ in acetone-$d_6$. Electron impact (EI) mass spectra were obtained with a Micromass AutoSpec (Beverly, Mass.) instrument. HPLC was performed on a Waters Associates liquid chromatograph equipped with a model 6000A solvent delivery system, model U6K Universal injector, and model 486 tunable absorbance detector. Solvents were dried and distilled following standard procedures.

The purity of final compounds was determined by HPLC, and they were judged at least 99% pure. Two HPLC columns (9.4 mm×25 cm Zorbax-Sil and Zorbax RX-C18) were used as indicated in Table 1 (Supporting Information). The purity and identity of the synthesized vitamins were additionally confirmed by inspection of their $^1$H NMR and high-resolution mass spectra.

(8S,20R)-des-A,B-20-(Formylmethyl)-8β-[(triethylsilyl) oxy]pregnane (9)

Diisobutylaluminium hydride (1.0 M in toluene, 1.3 mL, 0.18 g, 1.3 mmol) was added to a solution of cyanide 7 (0.22 g, 0.66 mmol) in dichloromethane (6 mL) at −10° C. The reaction mixture was stirred at −10° C. for 1 h, then it was quenched with a saturated aqueous sodium potassium tartrate solution (5 mL). The water phase was extracted with dichloromethane. Combined organic layers were washed with brine, dried ($Na_2SO_4$) and concentrated to give aldehyde 9 (0.20 g, 90% yield).

(8S,20S)-des-A,B-20-(Formylmethyl)-8β-[(triethylsilyl) oxy]pregnane (10)

Reaction of cyanide 8 with diisobutylaluminium hydride, carried out as described for 9, gave aldehyde 10 (48 mg, 99% yield %).

(8S,20R)-des-A,B-20-(2'R- and 2'S-Hydroxy-3',3'-difluoro-3'-ethoxycarbonyl-propyl)-8β-[(triethylsilyl)oxy] pregnane (11a,b). Samarium (II) iodide (0.07-0.12 M in THF, 20 mL, 0.97 g, 2.4 mmol) was added to a solution of aldehyde 9 (0.20 g, 0.59 mmol) and ethyl bromodifluoroacetate (0.085 mL, 0.13 g, 0.66 mmol). The reaction mixture was stirred under argon at room temperature for 1 h, diluted with water and extracted with ethyl acetate. Combined organic phases were dried ($Na_2SO_4$) and concentrated. The residue was purified by column chromatography on silica gel (10% ethyl acetate/hexane) to give esters 11a,b (0.12 g, 45% yield).

(8S,20S)-des-A,B-20-(2'R- and 2'S-Hydroxy-3',3'-difluoro-3'-ethoxycarbonyl-propyl)-8β-[(triethylsilyl)oxy] pregnane (12a,b). Reaction of aldehyde 10 with ethyl bromodifluoroacetate and samarium (II) iodide, carried out as described for 11a,b, gave esters 12a,b (43 mg, 66% yield).

(8S,20R)-des-A,B-20-[2'R- and 2'S—O-(1H-imidazol-1-ylcarbonothionyl)-3',3'-difluoro-3'-ethoxycarbonylpropyl]-8β-[(triethylsilyl)oxy]pregnane (13a,b). 1,1'-Thiocarbonyldiimidazole (0.15 g, 0.84 mmol) was added to a solution of ester 11a,b (0.12 g, 0.26 mmol) in THF (6 mL). The reaction mixture was stirred at room temperature for 3 days, diluted with water and extracted with ethyl acetate. Combined organic phases were dried ($Na_2SO_4$) and concentrated. The residue was purified by column chromatography on silica gel (5%, then 10% and 20% ethyl acetate/hexane) to give thionocarbonates 13a,b (0.13 g, 89% yield).

(8S,20S)-des-A,B-20-[2'R- and 2'S—O-(1H-imidazol-1-ylcarbonothionyl)-3',3'-difluoro-3'-ethoxycarbonylpropyl]-8β-[(triethylsilyl)oxy]pregnane (14a,b). Reaction of ester 12a,b with 1,1'-thiocarbonyldiimidazole, carried out as described for 13a,b, gave esters 14a,b (35 mg, 66% yield).

(8S,20R)-des-A,B-20-(3',3'-Difluoro-3'-ethoxycarbonylpropyl)-8β-[(triethylsilyl)oxy]pregnane (15). Triethylsilane (2 mL, 1.46 g, 12.5 mmol) was added to thionocarbonates 13a,b (0.13 g, 0.23 mmol) under argon. Benzoyl peroxide (23 mg, 0.095 mmol) dissolved in toluene (0.3 mL) was added in 3 portions. The reaction was stirred at 115° C. for 2.5 h, then cooled to room temperature and concentrated. The crude product was applied to a Waters silica Sep-Pak cartridge (5 g). Elution with ethyl acetate/hexane (3:97, then 5:95) gave ester 15 (92 mg, 92% yield).

(8S,20S)-des-A,B-20-(3',3'-Difluoro-3'-ethoxycarbonylpropyl)-8β-[(triethylsilyl)oxy]pregnane (16). Reaction of esters 14a,b with triethylsilane and benzoyl peroxide, carried out as described for 15, gave ester 16 (27 mg, 99% yield).

(8S,20R)-des-A,B-24,24-Difluoro-8β-[(triethylsilyl)oxy] cholestan-25-ol (17). Methylmagnesium bromide (3.0 M solution in diethyl ether, 0.15 mL, 0.45 mmol) was added to a solution of the ester 15 (92 mg, 0.21 mmol) in anhydrous THF (3 mL) at 0° C. The reaction mixture was stirred at 0° C. for 1 h, then quenched with water, extracted with ethyl acetate, dried ($Na_2SO_4$), and concentrated. The residue was applied on a Waters silica Sep-Pak cartridge (10 g). Elution with ethyl acetate/hexane (5:95) gave alcohol 17 (80 mg, 90% yield).

(8S,20S)-des-A,B-24,24-Difluoro-8β-[(triethylsilyl)oxy] cholestan-25-ol (18). Reaction of ester 16 with methylmagnesium bromide, carried out as described for 17, gave ester 18 (29 mg, 97% yield).

(8S,20R)-des-A,B-24,24-Difluorocholestane-8β,25-diol (19). Tetrabutylammonium fluoride (1.0 M in THF, 3 mL, 3 mmol) was added to a solution of alcohol 17 (80 mg, 0.18 mmol) in THF (4 mL) at 0° C. The reaction mixture was stirred at room temperature for 4 h. Then it was diluted with water and extracted with ethyl acetate. The combined organic extracts were dried ($Na_2SO_4$) and concentrated. The crude product was applied to a Waters silica Sep-Pak cartridge (5 g). Elution with ethyl acetate/hexane (5:95, then 10:90 and 20:80) gave diol 19 (59 mg, 100% yield).

(8S,20S)-des-A,B-24,24-Difluorocholestane-8β,25-diol (20). Reaction of alcohol 18 with tetrabutylammonium fluoride, carried out as described for 19, gave diol 20 (21 mg, 98% yield).

(20R)-des-A,B-24,24-Difluoro-25-[(triethylsilyl)oxy] cholestan-8-one (21). Molecular sieves (4 Å, 60 mg) were added to a solution of 4-methylmorpholine oxide (60 mg, 0.51 mmol) in dichloromethane (0.5 mL). The mixture was stirred at room temperature for 15 min, and tetrapropylammonium perruthenate (4 mg, 11.4 mol) was added, followed by a solution of the diol 19 (31.6 mg, 0.11 mmol) in dichloromethane (500+300 μL). The resulting suspension was stirred at room temperature for 1 h. The reaction mixture was filtered through a Waters silica Sep-Pak cartridge (2 g) that was further washed with ethyl acetate to give the 25-hydroxy-8-ketone 21a (31 mg, 99%).

Triethylsilyl trifluoromethanesulfonate (30 μL, 35 mg, 132 μmol) was added dropwise to a solution of the obtained 25-hydroxy-8-ketone 21a (31 mg, 98 mol) and 2.6-lutidine (30 μL, 28 mg, 0.26 mmol) in dichloromethane (2 mL) at −40° C. The reaction mixture was stirred at −40° C. for 15 min. Then it was diluted with dichloromethane and washed with water. The organic layer was dried ($Na_2SO_4$) and concentrated. The residue was applied on a Waters silica Sep-Pak cardridge (5 g). Elution with ethyl acetate/hexane (3:97, then 10:90) gave the protected ketone 21 (19.8 mg, 46%).

(20S)-des-A,B-24,24-Difluoro-25-[(triethylsilyl)oxy] cholestan-8-one (22). Oxidation of the diol 20 with tetrapropylammonium perruthenate and 4-methylmorpholine oxide, and the subsequent silylation of the resulted 25-hydroxy-8-ketone was performed as described for conversion of 19 into 21. The protected ketone 22 was obtained in 82% yield.

(20R)-1α,25-Dihydroxy-24,24-difluoro-2-methylene-19-norvitamin $D_3$ (3). Phenyllithium (1.8 M in di-n-buthylether, 77 μL, 11.6 mg, 138 μmol) was added to a stirred solution of the phosphine oxide A (80 mg, 137 μmol) in anhydrous THF (500 μL) at −30° C. After 30 min the mixture was cooled to −78° C. and a precooled solution of the ketone 21 (19.8 mg, 46 μmol) in anhydrous THF (300+200 μL) was added. The reaction mixture was stirred under argon at −78° C. for 4 hours and then at +4° C. for 19 h. Ethyl acetate was added and the organic phase was washed with brine, dried ($Na_2SO_4$) and concentrated. The residue was applied to a Waters silica Sep-Pak cartridge (5 g). The cartridge was washed with hexane and ethyl acetate/hexane (1:99) to give the protected vitamin 23 (22.2 mg, 61% yield).

The protected compound 23 (22.1 mg, 27.8 μmol) was dissolved in THF (3 mL) and acetonitrile (3 mL). A solution of aqueous 48% HF in acetonitrile (1:9 ratio, 4 mL) was added at 0° C. and the resulting mixture was stirred at room temperature for 2 h. Saturated aqueous $NaHCO_3$ solution was added and the reaction mixture was extracted with dichloromethane. The combined organic phases were dried ($Na_2SO_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product 3. The vitamin 3 was further purified by straight phase HPLC [9.4×250 mm Zorbax Silica column, 5 mL/min, hexane/2-propanol (85:15) solvent system, $R_f$=5.1 min.] and reverse phase HPLC [9.4×250 mm Zorbax RX-C18 column, 4 mL/min, methanol/water (80:20) solvent system, $R_f$=12.5 min.] to give the pure compound 3 (8.96 mg, 72% yield). Pure crystals of the analogue 3 were obtained after crystallization from hexane/2-propanol and they were characterized by an X-ray analysis.

(20S)-1α,25-Dihydroxy-24,24-difluoro-2-methylene-19-norvitamin $D_3$ (4). The protected vitamin 24 was prepared in 59% yield by the Wittig-Horner reaction of the ketone 22 and the phosphine oxide A, performed analogously to the process described above for the preparation of 23. The protected vitamin 24 was hydrolyzed as described for 23, and the product 4 was further purified by a normal-phase HPLC [9.4 mm×25 cm Zorbax Silica column, 4 mL/min, hexane/2-propanol (85:15) solvent system, $R_f$=8.4 min.] and a reversed-phase HPLC [9.4×25 cm Zorbax RX-C18 column, 3 mL/min, methanol/water (85:15) solvent system, $R_f$=8.7 min] to give the pure compound 4 (3.5 mg, 79%).

(20R)-1α,25-Dihydroxy-24,24-difluoro-19-norvitamin $D_3$ (5). The protected vitamin 25 was prepared in 29% yield by the Wittig-Horner reaction of the ketone 21a and the phosphine oxide B, performed analogously to the process described above for the preparation of 23. The protected vitamin 25 was hydrolyzed as described for 23, and the product 5 was further purified by a normal-phase HPLC [9.4 mm×25 cm Zorbax Silica column, 5 mL/min, hexane/2-propanol (85:15) solvent system, $R_f$=7.7 min.] and a reversed-phase HPLC [9.4×25 cm Zorbax RX-C18 column, 3 mL/min, methanol/water (85:15) solvent system, $R_f$=8.2 min] to give the pure compound 5 (6.7 mg, 59%). Pure crystals of the analogue 5 were obtained after crystallization from hexane/2-propanol and they were characterized by an X-ray analysis.

(20S)-1α,25-Dihydroxy-24,24-difluoro-19-norvitamin $D_3$ (6). The protected vitamin 26 was prepared from the ketone 22 in 58% yield analogously to the isomeric vitamin 25. Hydrolysis of silyl protecting groups in 26 was performed as described for 23 and the obtained vitamin 6 was purified by a normal-phase HPLC [9.4 mm×25 cm Zorbax-Sil column, 5 mL/min, hexane/2-propanol (85:15) solvent system, $R_f$=8.1 min] and a reversed-phase HPLC [9.4 mm×25 cm Zorbax RX-C18 column, 4 mL/min, methanol/water (85:15) solvent system, $R_f$=5.8 min] to give the pure compound 6 (2.5 mg, 23%).

Biological Studies

1. In vitro Studies. VDR binding, HL-60 differentiation, and 24-hydroxylase transcription assays were performed as previously described and are shown in the footnote of Table 1.[16,25]

2. In vivo Studies. Bone calcium mobilization and intestinal calcium transport.

Male, weanling Sprague-Dawley rats were purchased from Harlan (Indianapolis, Ind.). The animals were group housed and placed on Diet 11 (0.47% Ca)+AEK oil for one week followed by Diet 11 (0.02% Ca)+AEK oil for 3 weeks. The rats were then switched to a diet containing 0.47% Ca[26] for one week followed by two weeks on a diet containing 0.02% Ca. Dose administration began during the last week on 0.02% Ca diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for the intestinal calcium transport analysis using the everted gut sac method.[25]

Crystallographic Studies

Crystal data for compound 3. $C_{27}H_{42}F_2O_3$, M=452.61, T=100 (1) K, monoclinic, C2, a=23.845 (5) Å, b=6.2760 (13) Å, c=20.711 (4) Å, αγ=90°, β=126.52 (3)°, V=2490.9 (9) Å$^3$, Z=4, $D_x$=1.207 Mg/m$^3$, μ=0.701 mm$^{-1}$, F (000)=984.

Crystal data for compound 5. $C_{26}H_{42}F_2O_3$, M=440.60, T=298 (2) K, monoclinic, C2, a=23.882 (5) Å, b=6.1654 (12) Å, c=19.632 (4) Å, αγ=90°, β=121.83 (3)°, V=2456.0 (8) Å$^3$, Z=4, $D_x$=1.192 Mg/m$^3$, μ=0.696 mm$^{-1}$, F (000)=960.

Structure determination. The data were collected using a Bruker AXS Platinum 135 CCD detector controlled with the PROTEUM software suite (Bruker AXS Inc., Madison, Wis.). The X-ray source was CuK radiation (1.54178 Å) from a Rigaku RU200 X-ray generator equipped with Montel optics, operated at 50 kV and 90 mA. The X-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as series of phi and omega oscillation frames each of 1° for 5-20 sec/frame. The detector was operated in 512×512 mode and was positioned 4.5 cm from the sample. Cell parameters were determined from a non-linear least squares fit in the range of 4.0<theta<55°.

The space group was determined by systematic absences and statistical tests and verified by subsequent refinement. The structure was solved by direct methods[27] and refined by the full-matrix least-squares methods on F$^2$. The hydrogen atom positions were determined from difference peaks and ultimately refined by a riding model with idealized geometry. Non-hydrogen atoms were refined with anisotropic displacement parameters. The absolute structure was determined by refinement of the Flack parameter.[28]

Crystallographic data for the structures reported in this paper have been deposited at the Cambridge Crystallographic Data Center with the deposition numbers: CCDC 1402441 (3) and CCDC 1402442 (5).

Purity criteria for the synthesized vitamin D compounds. All vitamin D analogs synthesized by us gave single sharp peaks on HPLC and they were judged at least 99% pure. Two HPLC systems (straight- and reversed-phase) were employed as indicated in the Table 2. The purity and identity of the synthesized vitamins were additionally confirmed by inspection of their $^1$H NMR and high-resolution mass spectra.

TABLE 2

Purity Criteria for Target Vitamin D Compounds

| Compound | Compd. No. | Straight-phase[a] (hexane/2-propanol) | Reversed-phase[b] (methanol/water) |
|---|---|---|---|
| (20R)-1α,25-Dihydroxy-24,24-difluoro-2-methylene-19-norvitamin $D_3$ | 3 | h/p (85:15) 25.5 mL | m/w (80:20) 50.0 mL |
| (20R)-1α,25-Dihydroxy-24,24-difluoro-19-norvitamin $D_3$ | 4 | h/p (85:15) 38.5 mL | m/w (85:15) 24.6 mL |
| (20S)-1α,25-Dihydroxy-24,24-difluoro-2-methylene-19-norvitamin $D_3$ | 5 | h/p (85:15) 33.6 mL | m/w (85:15) 26.1 mL |
| (20S)-1α,25-Dihydroxy-24,24-difluoro-19-norvitamin $D_3$ | 6 | h/p (85:15) 40.5 mL | m/w (85:15) 23.2 mL |

[a]Zorbax-Sil 9.4 mm × 25 cm column.
[b]Zorbax RX-C18 9.4 mm × 25 cm column.

Spectral Data of the Synthesized Compounds (8S,20R)-des-A,B-20-(Formylmethyl)-8β-[(triethylsilyl)oxy]pregnane (9): [α]$_D$+33.3° (c 0.95, CHCl$_3$); $^1$H NMR (400 MHz, CDCl$_3$) δ 9.74 (1H, dd, J=3.4, 1.1 Hz), 4.03 (1H, d, J=2.1 Hz), 2.45 (1H, dd, J=15.5, 2.0 Hz), 2.13 (1H, ddd, J=9.2, 3.5 Hz), 1.95 (1H, m), 0.99 (3H, d, J=6.5 Hz), 0.954 (3H, s), 0.948 (9H, t, J=7.9 Hz), 0.55 (6H, q, J=7.9 Hz); $^{13}$C NMR (100 MHz, CDCl$_3$) δ 203.66 (1), 69.24 (1), 56.54 (1), 53.05 (1), 50.78 (2), 42.26 (0), 40.61 (2), 34.51 (2), 31.26

(1), 27.56 (2), 22.91 (2), 19.92 (3), 17.60 (2), 13.50 (3), 6.92 (3), 4.91 (2); MS (EI) m/z 338 (5, M$^+$), 309 (100, M$^+$-Et), 295 (14), 281 (6), 251 (4), 225 (8), 189 (18), 163 (32), 133 (7), 107 (10), 102 (35), 75 (21); MS (ESI) m/z 361 (20, [M+Na]$^+$), 699 (100, [2M+Na]$^+$), 1037 (15, [3M+Na]$^+$); exact mass calculated for C$_{21}$H$_{42}$O$_3$SiNa [M+CH$_3$OH+Na]$^+$ 393.2796, found 393.2800.

(8S,20S)-des-A,B-20-(Formylmethyl)-8β-[(triethylsilyl)oxy]pregnane (10): [α]$_D$ +41.4° (c 0.72, CHCl$_3$); $^1$H NMR (400 MHz, CDCl$_3$) δ 9.74 (1H, dd, J=3.5, 1.0 Hz), 4.03 (1H, d, J=2.4 Hz), 2.65 (1H, dd, J=15.8, 3.1 Hz), 2.20 (1H, ddd, J=15.8, 9.6, 3.7 Hz), 2.00 (1H, m), 0.95 (9H, t, J=7.9 Hz), 0.95 (3H, s), 0.91 (3H, d, J=6.9 Hz), 0.55 (6H, q, J=7.9 Hz); $^{13}$C NMR (100 MHz, CDCl$_3$) δ 203.46 (1), 69.21 (1), 56.19 (1), 52.98 (1), 49.92 (2), 42.17 (0), 40.74 (2), 34.47 (2), 30.25 (1), 27.03 (2), 22.74 (2), 19.73 (3), 17.62 (2), 13.98 (3), 6.93 (3), 4.93 (2); MS (EI) m/z 338 (4, M$^+$), 309 (100, M$^+$-Et), 295 (15), 281 (6), 251 (12), 225 (20), 205 (13), 189 (28), 163 (38), 147 (13), 133 (17), 103 (64), 87 (25), 75 (32); MS (ESI) m/z 339 (1, [M+H]$^+$); exact mass calculated for C$_{20}$H$_{39}$O$_2$Si [M+H]$^+$ 339.2714, found 339.2703.

(8S,20R)-des-A,B-20-(2'R- and 2'S-Hydroxy-3',3'-difluoro-3'-ethoxycarbonylpropyl)-8β-[(triethylsilyl)oxy]pregnane (11a,b): $^1$H NMR (400 MHz, CDCl$_3$) δ 4.35 (2H, dq, J=7.0 Hz), 4.12 (1H, q, J=6.8 Hz), 4.03 (1H, bs), 1.36 (3H, t, J=7.0 Hz), 1.03 (3H, d, J=6.5 Hz), 0.945 (9H, t, J=7.9 Hz), 0.935 (3H, s), 0.55 (6H, q, J=7.9 Hz); $^{13}$C NMR (100 MHz, CDCl$_3$) δ 163.77 (t, $^2$J$_{FC}$=31.2 Hz, C=O), 114.92 (t, $^1$J$_{FC}$=255.5 Hz, CF$_2$), 71.21 (t, $^2$J$_{FC}$=25.9 Hz, 1), 69.22 (t, $^2$J$_{FC}$=25.9 Hz, 1), 62.94 (2), 57.20 (1), 56.97 (1), 53.09 (1), 52.95 (1), 42.28 (0), 42.24 (0), 40.75 (2), 40.67 (2), 36.22 (2), 34.55 (2), 34.04 (1), 31.32 (1), 27.40 (2), 22.97 (2), 22.92 (2), 19.63 (3), 18.17 (3), 17.62 (2), 13.90 (3), 13.51 (3), 13.33 (3), 6.89 (3), 4.89 (2); $^{19}$F NMR (376 MHz, CDCl$_3$) δ–113.98 (dd, J=263.0, 8.0 Hz), –114.87 (dd, J=263.0, 8.0 Hz), –121.25 (dd, J=98.5, 14.8 Hz), –121.95 (dd, J=98.5, 14.8 Hz); MS (EI) m/z no M$^+$, 448 (4), 419 (100), 405 (34), 315 (55), 225 (28), 163 (56), 135 (67), 102 (90), 102 (35), 75 (52); MS (ESI) m/z 485 (42, [M+Na]$^+$), 947 (100, [2M+Na]$^+$), 1409 (2, [3M+Na]$^+$); exact mass calculated for C$_{24}$H$_{44}$F$_2$O$_4$SiNa [M+Na]$^+$ 485.2870, found 485.2868.

(8S,20S)-des-A,B-20-(2'R- and 2'S-Hydroxy-3',3'-difluoro-3'-ethoxycarbonylpropyl)-8β-[(triethylsilyl)oxy]pregnane (12a,b): $^1$H NMR (400 MHz, CDCl$_3$) δ 4.35 (2H, dq, J=7.2 Hz, 2.0 Hz), 4.13 (1H, m), 4.08 (1H, m), 4.03 (1H, bs), 1.36 (3H, t, J=7.2 Hz), 0.94 (9H, t, J=7.9 Hz), 0.93 (3H, s), 0.88 (3H, d J=6.5 Hz), 0.55 (6H, q, J=7.9 Hz); $^{13}$C NMR (100 MHz, CDCl$_3$) δ 163.75 (t, $^2$J$_{FC}$=32.2 Hz, C=O), 114.91 (t, $^1$J$_{FC}$=255.0 Hz, CF$_2$), 71.32 (t, $^2$J$_{FC}$=25.9 Hz, 1), 69.69 (t, $^2$J$_{FC}$=25.9 Hz, 1), 69.29 (1), 62.99 (2), 57.12 (1), 56.82 (1), 53.08 (1), 52.94 (1), 42.13 (0), 41.00 (2), 40.67 (2), 35.97 (2), 34.53 (2), 32.41 (1), 34.41 (2), 30.46 (1), 27.38 (2), 26.10 (2), 22.83 (2), 19.33 (3), 17.94 (3), 17.66 (2), 14.03 (3), 13.92 (3), 13.83 (3), 6.91 (3), 4.91 (2); $^{19}$F NMR (376 MHz, CDCl$_3$) δ–113.74 (dd, J=262.0, 8.0 Hz), –114.40 (dd, J=262.0, 8.0 Hz), –120.88 (dd, J=262.0, 14.0 Hz), –121.23 (dd, J=262.0, 14.0 Hz); MS (EI) m/z no M$^+$, 448 (6), 419 (100), 405 (24), 315 (20), 225 (23), 163 (27), 135 (30), 102 (53), 87 (24), 75 (28); MS (ESI) m/z 485 (100, [M+Na]$^+$), 947 (55, [2M+Na]$^+$); exact mass calculated for C$_{24}$H$_{44}$F$_2$O$_4$SiNa [M+Na]$^+$ 485.2870, found 485.2868.

(8S,20R)-des-A,B-20-[2'R- and 2'S—O-(1H-imidazol-1-ylcarbonothionyl)-3',3'-difluoro-3'-ethoxycarbonylpropyl]-8β-[(triethylsilyl)oxy]pregnane (13a,b): $^1$H NMR (400 MHz, CDCl$_3$) δ 8.34 and 8.32 (1H, s), 7.63 and 7.61 (1H, s), 7.07 and 7.05 (1H, s), 6.23 (1H, m, J=11.0, 7.2 Hz), 4.30 (2H, q, J=7.0 Hz), 4.02 (1H, bs), 1.28 (3H, dt, J=7.0 Hz), 0.94 (9H, t, J=7.9 Hz), 0.92 (3H, d, J=5.0 Hz), 0.85 (3H, s), 0.55 (6H, dq, J=7.9 Hz); $^{13}$C NMR (100 MHz, CDCl$_3$) δ 183.37 (C=S), 182.28 (C=S), 162.08 (t, $^2$J$_{FC}$=31.2 Hz, C=O), 137.04 (1), 131.18 (1), 131.15 (1), 118.13 (1), 117.92 (1), 113.03 (t, $^1$J$_{FC}$=255.5 Hz, CF$_2$), 78.76 (dd, $^2$J$_{FC}$=28.9, 25.6 Hz, 1), 77.53 (dd, $^2$J$_{FC}$=28.9, 25.6 Hz, 1), 69.15 (1), 63.58 (2), 56.99 (1), 56.44 (1), 52.98 (1), 52.91 (1), 42.21 (0), 40.63 (2), 40.55 (2), 34.42 (2), 33.90 (2), 33.79 (2), 32.70 (1), 31.58 (1), 27.58 (2), 27.27 (2), 22.84 (2), 19.17 (3), 18.82 (3), 17.54 (2), 13.74 (3), 13.43 (3), 13.33 (3), 6.88 (3), 4.86 (2); $^{19}$F NMR (376 MHz, CDCl$_3$) δ–112.45 (dd, J=264.0, 8.6 Hz), –114.08 (dd, J=264.0, 8.6 Hz), –116.29 (dd, J=264.0, 12.5 Hz), –116.91 (dd, J=264.0, 12.5 Hz); MS (ESI) m/z 573 (100, [M+H]$^+$), 595 (20, [M+Na]$^+$), 1145 (85, [2M+H]$^+$); exact mass calculated for C$_{28}$H$_{47}$F$_2$O$_4$N$_2$SSi [M+H]$^+$ 573.2989, found 573.2971.

(8S,20S)-des-A,B-20-[2'R- and 2'S—O-(1H-imidazol-1-ylcarbonothionyl)-3',3'-difluoro-3'-ethoxycarbonylpropyl]-8β-[(triethylsilyl)oxy]pregnane (14a,b): $^1$H NMR (400 MHz, CDCl$_3$) δ 8.34 and 8.32 (1H, s), 7.63 and 7.60 (1H, s), 7.07 and 7.05 (1H, s), 6.28 (1H, q, J=10.6 Hz), 6.17 (JH, in, J=7.2, 6.2 Hz), 4.30 (2H, m, J=7.1 Hz), 4.02 (1H, bs), 1.28 (3H, t, J=7.1 Hz), 0.95 (3H, d, J=5.2 Hz), 0.94 (9H, t, J=7.9 Hz), 0.83 (3H, s), 0.54 (6H, q, J=7.9 Hz); $^{13}$C NMR (125 MHz, CDCl$_3$) δ 183.32 (C=S), 182.24 (C=S), 162.14 (t, $^2$J$_{FC}$=31.2 Hz, C=O), 137.16 (1), 131.25 (1), 131.16 (1), 118.07 (1), 118.00 (1), 112.56 (t, $^1$J$_{FC}$=256.2 Hz, CF$_2$), 79.00 (dd, $^2$J$_{FC}$=28.6, 25.6 Hz, 1), 77.71 (dd, $^2$J$_{FC}$=28.6, 25.6 Hz, 1), 69.13 (1), 63.66 (2), 57.22 (1), 56.61 (1), 52.98 (1), 52.91 (1), 42.11 (0), 41.18 (2), 40.98 (2), 34.45 (2), 34.40 (2), 31.73 (1), 30.51 (1), 27.40 (2), 26.71 (2), 22.73 (2), 22.65 (2), 18.91 (3), 18.89 (3), 17.64 (2), 13.95 (3), 13.78 (3), 13.76 (3), 6.92 (3), 4.86 (2); $^{19}$F NMR (376 MHz, CDCl$_3$) δ–112.45 (dd, J=265.0, 9.0 Hz), –114.08 (dd, J=264.0, 9.0 Hz), –116.29 (dd, J=264.0, 12.5 Hz), –116.91 (dd, J=265.0, 12.5 Hz); MS (ESI) m/z 573 (100, [M+H]$^+$), 595 (15, [M+Na]$^+$), 1145 (23, [2M+H]$^+$); exact mass calculated for C$_{28}$H$_{47}$F$_2$O$_4$N$_2$SSi [M+H]$^+$ 573.2989, found 573.2982.

(8S,20R)-des-A,B-20-(3',3'-Difluoro-3'-ethoxycarbonylpropyl)-8β-[(triethylsilyl)oxy]pregnane (15): [α]$_D$ +35.0 (c 1.0, CHCl$_3$); $^1$H NMR (400 MHz, CDCl$_3$) δ 4.32 (2H, q, J=7.1 Hz), 4.03 (1H, bs), 2.10 (1H, m), 1.35 (3H, t, J=7.1 Hz), 0.94 (9H, t, J=7.9 Hz), 0.91 (3H, d, J=4.5 Hz), 0.90 (3H, s), 0.55 (6H, q, J=7.9 Hz); $^{13}$C NMR (100 MHz, CDCl$_3$) δ 164.43 (t, $^2$J$_{FC}$=32.2 Hz, C=O), 116.79 (t, $^1$J$_{FC}$=250.0 Hz, CF$_2$), 69.30 (1), 62.63 (2), 56.05 (1), 53.04 (1), 42.12 (0), 40.71 (2), 34.57 (2), 34.54 (1), 31.12 (t, $^2$J$_{FC}$=23.0 Hz, 2), 27.07 (2), 22.92 (2), 18.29 (3), 17.64 (2), 13.97 (3), 13.49 (3), 6.91 (3), 4.91 (2); $^{19}$F NMR (376 MHz, CDCl$_3$) δ–104.85 (t, J=16.5 Hz), –105.5 (t, J=16.5 Hz), –105.7 (t, J=16.8 Hz), –106.3 (t, J=16.8 Hz); MS (EI) m/z 446 (5, M$^+$), 417 (67, M$^+$-Et), 403 (50), 389 (4), 313 (54), 295 (100), 281 (5), 241 (7), 225 (25), 201 (6), 177 (42), 163 (35), 135 (76), 121 (28), 102 (78), 75 (38); MS (ESI) m/z 447 (5, [M+H]$^+$), 469 (22, [M+Na]$^+$), 915 (100, [2M+Na]$^+$), 1361 (1, [3M+Na]$^+$); exact mass calculated for C$_{24}$H$_{45}$F$_2$O$_3$Si [M+H]$^+$ 447.3101, found 447.3092.

(8S,20S)-des-A,B-20-(3',3'-Difluoro-3'-ethoxycarbonylpropyl)-8β-[(triethylsilyl)oxy]pregnane (16): [α]$_D$ +13.2 (c 1.0, CHCl$_3$); $^1$H NMR (400 MHz, CDCl$_3$) δ 4.32 (2H, dq, J=7.1, 0.8 Hz), 4.02 (1H, bd, J=2.4 Hz), 1.35 (3H, t, J=7.1 Hz), 0.94 (9H, t, J=7.9 Hz), 0.90 (3H, s), 0.83 (3H, d, J=6.6 Hz), 0.55 (6H, q, J=7.9 Hz); $^{13}$C NMR (100 MHz, CDCl$_3$) δ 164.49 (t, $^2$J$_{FC}$=32.2 Hz, C=O), 116.77 (t, $^1$J$_{FC}$=250.0 Hz, CF$_2$), 69.30 (1), 62.67 (2), 55.88 (1), 53.05 (1), 42.14 (0), 40.59 (2), 34.56 (2), 34.14 (1), 31.49 (t, $^2J_{FC}$=23.0 Hz, 2), 27.19 (2), 26.61 (2), 22.82 (2), 18.37 (3), 17.68 (2), 13.96 (3), 13.77 (3), 6.92 (3), 4.91 (2); $^{19}$F NMR (470 MHz, CDCl$_3$) δ −54.6 (t, J=16.9 Hz), −55.1 (t, J=16.9 Hz), −55.2 (t, J=16.9 Hz), −55.7 (t, J=16.9 Hz); MS (EI) m/z 446 (1, M$^+$), 432 (38), 403 (98), 389 (89), 299 (90), 281 (89), 225 (88), 177 (91), 163 (90), 135 (96), 121 (67), 103 (100), 87 (95), 75 (89); MS (ESI) m/z 469 (100, [M+Na]$^+$), 915 (92, [2M+Na]$^+$); exact mass calculated for C$_{24}$H$_{44}$F$_2$O$_3$SiNa [M+Na]$^+$ 469.2920. found 469.2923.

(8S,20R)-des-A,B-24,24-Difluoro-8β-[(triethylsilyl)oxy]cholestane-25-ol (17): $[\alpha]_D$ +34.1 (c 1.0, CHCl$_3$); $^1$H NMR (400 MHz, CDCl$_3$) δ 4.03 (1H, bs), 2.04 (1H, m), 0.95 (9H, t, J=7.9 Hz), 0.91 (3H, s), 0.90 (3H, d, J=5.2 Hz), 0.55 (6H, q, J=7.9 Hz); $^{13}$C NMR (100 MHz, CDCl$_3$) δ 125.53 (t, $^1J_{FC}$=247.5 Hz, CF$_2$), 73.36 (t, $^2J_{FC}$=27.5 Hz, C-25), 69.36 (1), 56.42 (1), 53.06 (1), 42.13 (0), 40.77 (2), 34.90 (1), 34.62 (2), 27.34 (t, $^2J_{FC}$=24.5 Hz, 2), 27.16 (2), 26.66 (2), 23.54 (3), 22.96 (2), 18.42 (3), 17.68 (2), 13.51 (3), 6.93 (3), 4.93 (2); $^{19}$F NMR (376 MHz, CDCl$_3$) δ−115.0 (dd, J=28.5, 10.0 Hz), −115.6 (dd, J=28.5, 10.0 Hz), −115.9 (dd, J=28.5, 10.0 Hz), −116.6 (dd, J=28.5, 10.0 Hz); MS (EI) m/z 432 (5, M$^+$), 403 (43, M$^+$-Et), 389 (45), 299 (38), 283 (20), 243 (12), 225 (31), 211 (7), 189 (14), 171 (18), 135 (100), 109 (22), 102 (71), 75 (34); MS (ESI) m/z 433 (4, [M+H]$^+$), 455 (12, [M+Na]$^+$), 887 (100, [2M+Na]$^+$); exact mass calculated for C$_{24}$H$_{46}$F$_2$O$_2$SiNa [M+Na]$^+$ 455.3128, found 455.3121.

(8S,20S)-des-A,B-24,24-Difluoro-8β-[(triethylsilyl)oxy]cholestane-25-ol (18): $[\alpha]_D$ +19.5 (c 1.0, CHCl$_3$); $^1$H NMR (500 MHz, CDCl$_3$) δ 4.03 (1H, bd, J=2.3 Hz), 1.96 (1H, m), 0.95 (9H, t, J=7.9 Hz), 0.92 (3H, s), 0.83 (3H, d, J=6.6 Hz), 0.55 (6H, q, J=7.9 Hz); $^{13}$C NMR (125 MHz, CDCl$_3$) δ 125.54 (t, $^1J_{FC}$=247.0 Hz, CF$_2$), 73.35 (t, $^2J_{FC}$=24.6 Hz, C-25), 69.37 (1), 56.10 (1), 53.10 (1), 42.18 (0), 40.57 (2), 34.62 (2), 34.46 (1), 27.45 (t, $^2J_{FC}$=24.5 Hz, 2), 27.23 (2), 26.16 (2), 23.53 (3), 22.88 (2), 18.49 (3), 17.74 (2), 13.77 (3), 6.93 (3), 4.93 (2); $^{19}$F NMR (470 MHz, CDCl$_3$) δ−113.8 (dd, J=28.2, 9.4 Hz), −114.3 (dd, J=28.2, 9.4 Hz), −114.5 (dd, J=28.2, 9.4 Hz), −115.0 (dd, J=28.2, 9.4 Hz); MS (EI) m/z 432 (7, M$^+$), 403 (55, M$^+$-Et), 389 (30), 299 (44), 283 (15), 225 (36), 171 (19), 135 (87), 103 (100), 87 (35), 75 (40), 59 (57); exact mass calculated for C$_{24}$H$_{46}$F$_2$O$_2$Si (M$^+$) 432.3230, found 432.3248.

(8S,20R)-des-A,B-24,24-Difluorocholestane-8β,25-diol (19): m.p 186-187° C.; $[\alpha]_D$ +26.5 (c 1.0, CHCl$_3$); $^1$H NMR (400 MHz, CDCl$_3$) δ 4.08 (1H, bs), 2.00 (1H, m), 1.30 (6H, s), 0.94 (3H, s), 0.92 (3H, d, J=6.5 Hz); $^{13}$C NMR (100 MHz, CDCl$_3$) δ 125.51 (t, $^1J_{FC}$=247.5 Hz, CF$_2$), 73.27 (t, $^2J_{FC}$=27.5 Hz, C-25), 69.30 (1), 56.25 (1), 52.53 (1), 41.82 (0), 40.32 (2), 34.88 (1), 33.48 (2), 27.29 (t, $^2J_{FC}$=24.6 Hz, 2), 26.998 (2), 26.60 (2), 23.53 (3), 22.44 (2), 18.32 (3), 17.38 (2), 13.49 (3); $^{19}$F NMR (376 MHz, CDCl$_3$) δ−114.9 (dd, J=28.5, 9.7 Hz), −115.6 (dd, J=28.5, 9.7 Hz), −115.9 (dd, J=28.5, 9.7 Hz), −116.5 (dd, J=28.5, 9.7 Hz); MS (EI) m/z 318 (5, M$^+$), 300 (11, M$^+$-H$_2$O), 285 (15), 263 (5), 227 (9), 204 (20), 193 (3), 163 (10), 135 (42), 111 (100), 81 (30), 59 (42); exact mass calculated for C$_{18}$H$_{32}$F$_2$O$_2$ (M$^+$) 318.2365, found 318.2357.

(8S,20S)-des-A,B-24,24-Difluorocholestane-8β,25-diol (20): $[\alpha]_D$ +9.7 (c 1.0, CHCl$_3$); $^1$H NMR (400 MHz, CDCl$_3$) δ 4.09 (1H, bs), 1.30 (6H, s), 0.95 (3H, s), 0.84 (3H, d, J=6.6 Hz); $^{13}$C NMR (125 MHz, CDCl$_3$) δ 125.51 (t, $^1J_{FC}$=247.6 Hz, CF$_2$), 73.27 (t, $^2J_{FC}$=27.0 Hz, C-25), 69.33 (1), 55.99 (1), 52.56 (1), 41.86 (0), 40.16 (2), 34.45 (1), 33.50 (2), 27.43 (t, $^2J_{FC}$=24.6 Hz, 2), 27.07 (2), 26.09 (2), 23.52 (3), 22.36 (2), 18.42 (3), 17.45 (2), 13.73 (3); $^{19}$F NMR (376 MHz, CDCl$_3$) δ−113.5 (dd, J=27.8, 10.2 Hz), −114.2 (dd, J=27.8, 10.2 Hz), −114.4 (dd, J=27.8, 10.2 Hz), −115.0 (dd, J=27.8, 10.2 Hz); MS (EI) m/z 318 (7, M$^+$), 300 (12, M$^+$-H$_2$O), 285 (26), 263 (8), 227 (37), 204 (40), 191 (53), 163 (28), 142 (60), 135 (87), 111 (99), 97 (77), 81 (86), 59 (93), 55 (100); MS (ESI) m/z 341 (7, [M+Na]$^+$), 659 (6, [2M+Na]$^+$); exact mass calculated for C$_{18}$H$_{32}$F$_2$O$_2$Na [M+Na]$^+$ 341.2263, found 341.2270.

(20R)-des-A,B-24,24-Difluoro-25-[(triethylsilyl)oxy]cholestan-8-one (21): $[\alpha]_D$ +1.9 (c 1.0, CHCl$_3$); $^1$H NMR (400 MHz, CDCl$_3$) δ 2.46 (1H, dd, J=11.6, 7.5 Hz), 1.29 (6H, s), 0.98 (3H, d, J=8.2 Hz), 0.95 (9H, t, J=7.9 Hz), 0.65 (3H, s), 0.60 (6H, q, J=7.9 Hz); $^{13}$C NMR (100 MHz, CDCl$_3$) δ 212.03 (C=O), 75.57 (C-25), 61.95 (1), 56.50 (1), 49.89 (0), 40.94 (2), 38.97 (2), 35.19 (1), 27.36 (2), 26.98 (t, $^2J_{FC}$=25.0 Hz, 2), 26.78 (2), 24.54 (3), 24.33 (3), 24.04 (2), 19.04 (2), 18.51 (3), 12.49 (3), 6.91 (3), 6.54 (2); $^{19}$F NMR (376 MHz, CDCl$_3$) δ−114.1 (dd, J=28.5, 9.2 Hz), −114.7 (dd, J=28.5, 9.2 Hz), −115.0 (dd, J=28.5, 9.2 Hz), −115.6 (dd, J=28.5, 9.2 Hz); MS (ESI) m/z 431 (7, [M+H]$^+$), 453 (85, [M+Na]$^+$), 883 (84, [2M+Na]$^+$), 1313 (100, [3M+Na]$^+$); exact mass calculated for C$_{24}$H$_{44}$F$_2$O$_2$SiNa [M+Na]$^+$ 453.2971, found 453.2982.

(20R)-des-A,B-24,24-Difluorocholestan-8-one (21a): $[\alpha]_C$ +1.0 (c 1.0, CHCl$_3$); $^1$H NMR (400 MHz, CDCl$_3$) δ 2.46 (1H, dd, J=11.3, 7.7 Hz), 1.31 (6H, s), 0.98 (3H, d, J=5.0 Hz), 0.65 (3H, s); $^{13}$C NMR (100 MHz, CDCl$_3$) δ 212.03 (C=O), 125.39 (t, $^1J_{FC}$=247.5 Hz, CF$_2$), 73.26 (t, $^2J_{FC}$=27.5 Hz, C-25), 61.87 (1), 56.28 (1), 49.84 (0), 40.89 (2), 38.89 (2), 35.10 (1), 27.35 (2), 27.26 (t, $^2J_{FC}$=24.6 Hz, 2), 26.67 (2), 23.99 (2), 23.51 (3), 19.00 (2), 18.50 (3), 12.45 (3); $^{19}$F NMR (376 MHz, CDCl$_3$) δ−114.8 (dd, J=28.8, 9.0 Hz), −115.5 (dd, J=28.8, 9.0 Hz), −115.8 (dd, J=28.8, 9.0 Hz), −116.5 (dd, J=28.8, 9.0 Hz); MS (EI) m/z 316 (15, M$^+$), 301 (18), 273 (25), 193 (5), 161 (7), 151 (43), 125 (100), 111 (98), 95 (36), 81 (77), 59 (54); MS (ESI) m/z 339 (8, [M+Na]$^+$), 655 (100, [2M+Na]$^+$), 972 (12, [3M+Na]$^+$); exact mass calculated for C$_{18}$H$_{30}$F$_2$O$_2$Na [M+Na]$^+$ 339.2107, found 339.2098.

(20S)-des-A,B-24,24-Difluoro-25-[(triethylsilyl)oxy]cholestan-8-one (22): $[\alpha]_D$ −13.9 (c 1.0, CHCl$_3$); $^1$H NMR (400 MHz, CDCl$_3$) δ 2.45 (1H, dd, J=11.4, 7.6 Hz), 1.29 (6H, s), 0.95 (9H, t, J=7.9 Hz), 0.87 (3H, d, J=6.2 Hz), 0.65 (3H, s), 0.60 (6H, q, J=7.9 Hz); $^{13}$C NMR (100 MHz, CDCl$_3$) δ 212.05 (C=O), 75.59 (C-25), 61.97 (1), 56.05 (1), 49.91 (0), 40.96 (2), 38.80 (2), 34.66 (1), 29.68 (2), 27.28 (t, $^2J_{FC}$=33.7 Hz, 2), 26.36 (2), 24.54 (3), 24.29 (3), 24.07 (2), 18.94 (2), 18.42 (3), 12.66 (3), 6.92 (3), 6.55 (2); $^{19}$F NMR (376 MHz, CDCl$_3$) δ−113.8 (dd, J=29.6, 7.5 Hz), −114.4 (dd, J=29.6, 7.5 Hz), −114.8 (dd, J=29.6, 7.5 Hz), −115.5 (dd, J=29.6, 7.5 Hz); MS (EI) m/z 430 (1, M$^+$), 401 (25, M$^+$-Et), 381 (32), 279 (95), 259 (45), 249 (17), 217 (24), 191 (37), 173 (100), 151 (47), 135 (42), 95 (40), 81 (66), 77 (54), 55 (44); MS (ESI) m/z 431 (65, [M+H]$^+$), 448 (100, [M+NH$_4$]$^+$), 878 (65, [2M+NH$_4$]$^+$); exact mass calculated for C$_{24}$H$_{48}$F$_2$O$_2$SiN [M+NH$_4$]$^+$ 448.3417, found 448.3408.

(20R)-1α-[(tert-Butyldimethylsilyl)oxy]-24,24-difluoro-25-[(triethylsilyl)oxy]-2-methylene-19-norvitamin D$_3$ tert-butyldimethylsilyl ether (23): UV (in hexane) λmax 262.5, 253.0, 245.0 nm; $^1$H NMR (400 MHz, CDCl$_3$) δ 6.22 (1H, d, J=11.1 Hz, 6-H), 5.84 (1H, d, J=11.1 Hz, 7-H), 4.97 (1H, s, =CH$_2$), 4.92 (1H, s, =CH$_2$), 4.42 (2H, m, 1β-H and 3α-H), 2.83 (1H, dm, J=11.9 Hz), 2.52 (1H, dd, J=13.2, 5.8 Hz, 10α-H), 2.46 (1H, dd, J=12.6, 4.3 Hz, 4α-H), 2.33 (1H, dd, J=13.2, 2.7 Hz, 10β-H), 2.18 (1H, dd, J=12.6, 8.8 Hz, 4β-H), 2.00 (2H, m), 1.299 and 1.290 (each 3H, each s, 26-H$_3$, 27-H$_3$), 0.95 (9H, t, J=7.9 Hz), 0.897 (9H, s, t-BuSi), 0.87 (3H, d, J=6.0 Hz), 0.86 (9H, s, t-BuSi), 0.60 (6H, q, J=7.9 Hz), 0.56 (3H, s, 18-H$_3$), 0.080 (3H, s, SiMe), 0.066 (3H, s, SiMe), 0.049 (3H, s, SiMe), 0.025 (3H, s, SiMe); $^{13}$C NMR (100 MHz, CDCl$_3$) δ 152.97 (0, C-2), 141.12 (0, C-8), 132.79 (0, C-5), 125.36 (t, $^1J_{FC}$=249.5 Hz, CF$_2$), 122.39 (1, C-6), 116.18 (1, C-7), 106.26 (2, =CH$_2$), 75.61 (t, $^2J_{FC}$=28.8 Hz, C-25, 0), 72.54 (1), 71.62 (1), 56.31 (1), 56.25 (1), 47.61 (2), 45.65 (0, C-13), 40.59 (2), 38.55 (2), 35.79 (1), 28.73 (2), 27.55 (2), 27.00 (t, $^2J_{FC}$=25.2 Hz, 2), 25.84 (3), 25.78 (3), 24.60 (3), 24.36 (3), 23.43 (2), 22.20 (2), 18.62 (3), 18.25 (0), 18.16 (0), 12.08 (3), 6.93 (3), 6.56 (2), −4.86 (3), −5.10 (3); $^{19}$F NMR (376 MHz, CDCl$_3$) δ−114.0 (dd, J=28.8, 9.1 Hz), −114.6 (dd, J=29.1, 8.8 Hz), −115.0 (dd, J=28.8, 8.8 Hz), −115.6 (dd, J=29.1, 9.1 Hz); MS (ESI) m/z 817 (2, [M+Na$^+$]); exact mass (ESI) calculated for C$_{45}$H$_{84}$F$_2$O$_3$Si$_3$Na [M+Na]$^+$ 817.5589, found 817.5623.

(20S)-1α-[(tert-Butyldimethylsilyl)oxy]-24,24-difluoro-25-[(triethylsilyl)oxy]-2-methylene-19-norvitamin D$_3$ tert-butyldimethylsilyl ether (24): UV (in hexane) λmax 262.5, 253.0, 245.0 nm; $^1$H NMR (400 MHz, CDCl$_3$) δ 6.22 (1H, d, J=11.1 Hz, 6-H), 5.84 (1H, d, J=11.1 Hz, 7-H), 4.97 (1H, s, =CH$_2$), 4.92 (1H, s, =CH$_2$), 4.42 (2H, m, 1β-H and 3α-H), 2.83 (1H, dm, J=11.0 Hz), 2.51 (1H, dd, J=13.3, 6.1 Hz, 10α-H), 2.46 (1H, dd, J=12.5, 4.2 Hz, 4α-H), 2.33 (1H, dd, J=13.3, 2.7 Hz, 10β-H), 2.18 (1H, dd, J=12.5, 8.6 Hz, 4β-H), 1.29 (6H, s, 26-H$_3$, 27-H$_3$), 0.95 (9H, t, J=7.9 Hz), 0.896 (9H, s, t-BuSi), 0.88 (3H, d, J=6.8 Hz), 0.86 (9H, s, t-BuSi), 0.60 (6H, q, J=7.9 Hz), 0.56 (3H, s, 18-H$_3$), 0.080 (3H, s, SiMe), 0.066 (3H, s, SiMe), 0.049 (3H, s, SiMe), 0.026 (3H, s, SiMe); $^{13}$C NMR (100 MHz, CDCl$_3$) δ 152.98 (0, C-2), 141.15 (0, C-8), 132.74 (0, C-5), 123.50 (t, $^1J_{FC}$=249.0 Hz, CF$_2$), 122.41 (1, C-6), 116.13 (1, C-7), 106.24 (2, =CH$_2$), 75.60 (t, $^2J_{FC}$=28.0 Hz, C-25, 0), 72.51 (1), 71.64 (1), 56.27 (1), 55.89 (1), 47.59 (2), 45.68 (0, C-13), 40.37 (2), 38.56 (2), 35.20 (1), 31.60 (3), 29.65 (3), 28.75 (2), 27.46 (2), 26.98 (t, $^2J_{FC}$=25.1 Hz, 2), 25.83 ( ), 25.77 (3), 23.43 (2), 22.09 (2), 18.54 (3), 18.24 (0), 18.16 (0), 12.23 (3), 6.92 (3), 6.55 (2), −4.87 (3), −4.91 (3), −5.11 (3); $^{19}$F NMR (376 MHz, CDCl$_3$) δ−113.0 (dd, J=30.2, 6.5 Hz), −113.7 (dd, J=30.2, 6.5 Hz), −114.1 (dd, J=30.2, 6.5 Hz), −114.8 (dd, J=30.2, 6.5 Hz); MS (ESI) m/z 817 (2, [M+Na$^+$]); exact mass (ESI) calculated for C$_{45}$H$_{84}$F$_2$O$_3$Si$_3$Na [M+Na]$^+$ 817.5589, found 817.5596.

(20R)-1α,25-Dihydroxy-24,24-difluoro-2-methylene-19-norvitamin D$_3$ (3): m.p. 163-164° C. (from hexane); UV (in EtOH) λ$_{max}$ 261.0, 252.0, 244.5 nm; $^1$H NMR (500 MHz, CDCl$_3$) δ 6.36 (1H, d, J=11.2 Hz, 6-H), 5.89 (1H, d, J=11.2 Hz, 7-H), 5.11 (1H, s, =CH$_2$), 5.09 (1H, s, =CH$_2$), 4.49 (2H, m, 1β-H and 3α-H), 2.86 (1H, dd, J=13.0, 4.5 Hz, 10β-H), 2.81 (1H, m, 9β-H), 2.57 (1H, dd, J=13.0, 3.0 Hz, 4α-H), 2.33 (1H, dd, J=13.0, 6.0 Hz, 4β-H), 2.29 (1H, dd, J=13.0 Hz, 8.5 Hz, 10α-H), 1.218 and 1.206 (each 3H, each s, 26-H$_3$, 27-H), 0.95 (3H, d, J=6.5 Hz, 21-H$_3$), 0.56 (3H, s, 18-H$_3$); $^{13}$C NMR (125 MHz, CDCl$_3$) δ 151.91 (0, C-2), 143.26 (0, C-8), 130.46 (0, C-5), 125.50 (t, $^1J_{FC}$=246.1 Hz, CF$_2$), 124.20 (1, C-6), 115.34 (1, C-7), 107.74 (2, =CH$_2$), 73.35 (t, $^2J_{FC}$=26.9 Hz, C-25, 0), 71.80 (1), 70.64 (1), 56.24 (1), 56.10 (1), 45.75 (0), 45.74 (2), 40.38 (2), 38.12 (2), 35.67 (1), 28.91 (2), 27.49 (2), 27.29 (t, $^2J_{FC}$=24.5 Hz, 2), 26.73 (2), 25.33 (3), 23.55 (3), 23.45 (2), 22.22 (2), 18.61 (3), 12.07 (3); MS (EI) m/z 444 (6, M$^+$), 426 (3, M$^+$-H$_2$O), 393 (2), 341 (2), 313 (6), 269 (5), 251 (6), 199 (6), 191 (15), 161 (10), 145 (19), 111 (43), 107 (100), 89 (80), 79 (78), 75 (43); $^{19}$F NMR (376 MHz, CDCl$_3$) δ−114.8 (dd, J=28.6, 10.0 Hz), −115.4 (dd, J=28.6, 10.0 Hz), −115.7 (dd, J=28.6, 10.0 Hz), −116.4 (dd, J=28.6, 10.0 Hz); MS (EI) m/z 452 (14, M$^+$), 434 (2, M$^+$-H$_2$O), 367 (9), 311 (3), 299 (10), 269 (8), 251 (6), 221 (4), 192 (12), 161 (7), 151 (11), 147 (17), 135 (19), 107 (19), 91 (100), 55 (22); MS (ESI) m/z 475 (100, [M+Na]$^+$), 927 (31, [2M+Na]$^+$), 1380 (3, [3M+Na]$^+$, exact mass (ESI) calculated for C$_{27}$H$_{42}$O$_3$F$_2$Na [M+Na]$^+$ 475.2995, found 475.3001.

(20S)-1α,25-Dihydroxy-24,24-difluoro-2-methylene-19-norvitamin D$_3$ (4): UV (in EtOH), λ$_{max}$ 261.0, 252.0, 244.5 nm; $^1$H NMR (400 MHz, CDCl$_3$) δ 6.36 (1H, d, J=11.2 Hz, 6-H), 5.89 (1H, d, J=11.2 Hz, 7-H), 5.11 (1H, s, =CH$_2$), 5.09 (1H, s, =CH$_2$), 4.49 (2H, m, 1β-H and 3α-H), 2.85 (1H, dd, J=13.2, 4.4 Hz, 10β-H), 2.82 (1H, dd, J=12.6, 3.8 Hz, 9β-H), 2.57 (1H, dd, J=13.3, 3.6 Hz, 4α-H), 2.33 (1H, dd, J=13.3, 6.1 Hz, 4β-H), 2.29 (1H, dd, J=13.2 Hz, 8.4 Hz, 10α-H), 1.31 (6H, s, 26-H$_3$, 27-H), 0.87 (3H, d, J=6.5 Hz, 21-H$_3$), 0.57 (3H, s, 18-H$_3$); $^{13}$C NMR (125 MHz, CDCl$_3$) δ 151.96 (0, C-2), 143.26 (0, C-8), 130.46 (0, C-5), 125.52 (t, $^1J_{FC}$=247.0 Hz, CF$_2$), 124.23 (1, C-6), 115.37 (1, C-7), 107.72 (2, =CH$_2$), 73.35 (t, $^2J_{FC}$=27.6 Hz, C-25, 0), 71.81 (1), 70.68 (1), 56.28 (1), 55.93 (1), 45.78 (0), 45.77 (2), 40.21 (2), 38.15 (2), 35.17 (1), 28.93 (2), 27.50 (t, $^2J_{FC}$=24.5 Hz, 2), 27.36 (2), 23.56 (3), 23.49 (3), 22.14 (2), 18.49 (3), 12.31 (3); MS (EI) m/z 444 (6, M$^+$), 426 (3, M$^+$-H$_2$O), 393 (2), 341 (2), 313 (6), 269 (5), 251 (6), 199 (6), 191 (15), 161 (10), 145 (19), 111 (43), 107 (100), 89 (80), 79 (78), 75 (43); $^{19}$F NMR (376 MHz, CDCl$_3$) δ−114.8 (dd, J=28.6, 9.4 Hz), −115.4 (dd, J=28.6, 9.4 Hz), −115.7 (dd, J=28.6, 9.4 Hz), −116.3 (dd, J=28.6, 9.4 Hz); MS (EI) m/z 452 (6, M$^+$), 450 (100), 431 (15), 415 (7), 397 (5), 362 (62), 346 (8), 306 (42), 294 (55), 265 (58), 247 (52), 241 (22), 189 (29), 158 (44), 144 (100), 132 (78), 105 (76), 93 (58), 78 (52); MS (ESI) m/z 470 (100, [M+NH$_4$]$^+$), 922 (24, [2M+NH$_4$]$^+$), exact mass (ESI) calculated for C$_{27}$H$_{46}$O$_3$F$_2$N [M+NH$_4$]$^+$ 470.3441, found 470.3447.

(20R)-1α-[(tert-Butyldimethylsilyl)oxy]-24,24-difluoro-25-[(triethylsilyl)oxy]-19-norvitamin D$_3$ tert-butyldimethylsilyl ether (25): UV (in hexane) λmax 260.5, 251.5, 243.5 nm; $^1$H NMR (400 MHz, CDCl$_3$) δ 6.17 (1H, d, J=11.1 Hz, 6-H), 5.82 (1H, d, J=11.1 Hz, 7-H), 4.10 (2H, m, 1β-H and 3α-H), 2.81 (1H, d, J=12.1 Hz), 2.38 (2H, dd, J=12.8, 7.4 Hz, 10α-H and 4α-H), 2.23 (1H, d, J=13.9 Hz, 10β-H), 2.10 (1H, m, 4β-H), 1.31 (6H, s, 26-H$_3$, 27-H$_3$), 0.95 (3H, d, J=6.4 Hz), 0.876 (9H, s, t-BuSi), 0.862 (9H, s, t-BuSi), 0.55 (3H, s, 18-H$_3$), 0.05 (12H, s, SiMe); $^{13}$C NMR (100 MHz, CDCl$_3$) δ 140.62 (0, C-8), 133.73 (0, C-5), 125.51 (t, $^1J_{FC}$=246.5 Hz, CF$_2$), 121.69 (1, C-6), 116.19 (1, C-7), 73.40 (t, $^2J_{FC}$=27.9 Hz, C-25, 0), 68.12 (1), 67.96 (1), 56.20 (1), 56.15 (1), 45.99 (2), 45.61 (0, C-13), 43.67 (2), 40.55 (2), 36.74 (2), 35.76 (1), 28.65 (2), 27.57 (2), 27.38 (t, $^2J_{FC}$=24.7 Hz, 2), 26.78 (2), 25.86 (3), 23.56 (3), 23.38 (2), 22.18 (2), 18.63 (3), 18.14 (0), 18.09 (0), 12.05 (3), −4.68 (3), −4.77 (3), −4.85 (3), −4.91 (3); $^{19}$F NMR (376 MHz, CDCl$_3$) δ−115.1 (dd, J=29.1, 9.0), −115.8 (dd, J=29.1, 9.0 Hz), −116.0 (dd, J=29.1, 9.0 Hz), −116.7 (dd, J=29.1, 9.0 Hz); MS (ESI) m/z 817 (7, [M+Na$^+$]); exact mass (ESI) calculated for C$_{38}$H$_{70}$F$_2$O$_3$Si$_2$Na [M+Na]$^+$ 691.4724, found 691.4721.

(20S)-1α-[(tert-Butyldimethylsilyl)oxy]-24,24-difluoro-25-[(triethylsilyl)oxy]-19-norvitamin D$_3$ tert-butyldimethylsilyl ether (26): UV (in hexane) λmax 262.0, 252.0, 243.5 nm; $^1$H NMR (400 MHz, CDCl$_3$) δ 6.17 (1H, d, J=11.1 Hz, 6-H), 5.82 (1H, d, J=11.1 Hz, 7-H), 4.07 (2H, m, 1β-H and 3α-H), 2.80 (1H, m), 1.29 (6H, s, 26-H$_3$, 27-H$_3$), 0.95 (9H, t, J=7.9 Hz), 0.87 (3H, d, J=4.4 Hz), 0.86 (18H, s, t-BuSi), 0.60 (6H, q, J=7.9 Hz), 0.55 (3H, s, 18-H$_3$), 0.05 (12H, m, SiMe); $^{13}$C NMR (100 MHz, CDCl$_3$) δ 140.73 (0, C-8), 133.66 (0, C-5), 124.05 (t, $^1J_{FC}$=249.0 Hz, CF$_2$), 121.74 (1, C-6), 116.15 (1, C-7), 75.58 (t, $^2J_{FC}$=28.0 Hz, C-25, 0), 67.96 (1), 67.82 (1), 56.26 (1), 55.87 (1), 45.98 (2), 45.65 (0), 45.39 (2), 43.70 (2), 43.59 (2), 37.57 (2), 36.79 (2), 35.21 (1), 28.71 (2), 27.48 (t, $^2J_{FC}$=25.2 Hz, 2), 25.82 (3), 24.57 (3), 24.32 (3), 23.42 (2), 22.11 (2), 18.56 (3), 18.10 (0), 12.22 (3), 6.93 (3), 6.55 (2), −4.66 (3), −4.75 (3), −4.83 (3); MS (ESI) m/z 805 (12, [M+Na$^+$]); exact mass (ESI) calculated for $C_{44}H_{84}F_2O_3Si_3Na$ [M+Na]$^+$ 805.5589, found 805.5598.

(20R)-1α,25-Dihydroxy-24,24-difluoro-19-norvitamin D$_3$ (5): m.p. 182-183° C. (from hexane); UV (in EtOH) λ$_{max}$ 260.0, 251.0, 243.0 nm; $^1$H NMR (500 MHz, CD$_3$OD) δ 6.22 (1H, d, J=11.2 Hz, 6-H), 5.90 (1H, d, J=11.2 Hz, 7-H), 4.04 and 3.99 (each 1H, each m, 1β-H and 3α-H), 2.84 (1H, dd, J=12.3, 3.6 Hz, 9β-H), 2.60 (1H, dd, J=13.5, 3.4 Hz, 10β-H), 2.41 (1H, dd, J=13.4, 3.0 Hz, 4α-H), 2.22 (1H, dd, J=13.4, 7.9 Hz, 4β-H), 2.17 (1H, dd, J=13.5, 6.5 Hz, 10α-H), 1.25 (6H, s, 26-H$_3$, 27-H), 0.97 (3H, d, J=6.5 Hz, 21-H$_3$), 0.59 (3H, s, 18-H$_3$); $^{13}$C NMR (125 MHz, CD$_3$OD) δ 141.97 (0, C-8), 133.92 (0, C-5), 126.78 (t, $^1J_{FC}$=247.5 Hz, CF$_2$), 123.42 (1, C-6), 117.20 (1, C-7), 73.71 (t, $^2J_{FC}$=27.3 Hz, C-25, 0), 67.97 (1), 67.69 (1), 57.64 (1), 57.46 (1), 46.78 (0, C-13), 45.40 (2), 42.65 (2), 41.85 (2), 37.62 (2), 37.13 (1), 29.80 (2), 28.59 (2), 28.39 (t, $^2J_{FC}$=24.8 Hz, 2), 28.10 (2), 24.51 (2), 23.93 (3), 23.85 (3), 23.27 (2), 19.19 (3), 12.42 (3); $^{19}$F NMR (376 MHz, CD$_3$OD) δ−114.0 (dd, J=28.0, 10.0 Hz), −114.7 (dd, J=28.0, 10.0 Hz), −114.9 (dd, J=28.0, 10.0 Hz), −116.4 (dd, J=28.0, 10.0 Hz); MS (EI) m/z 440 (7, M$^+$), 422 (1, M$^+$-H$_2$O), 299 (5), 275 (6), 207 (34), 182 (4), 147 (5), 125 (10), 107 (13), 91 (100), 81 (15), 65 (26); MS (ESI) m/z 463 (80, [M+Na]$^+$), 904 (14, [2M+Na]$^+$); exact mass (ESI) calculated for $C_{26}H_{42}O_3F_2Na$ [M+Na]$^+$ 463.2995, found 463.2998.

(20S)-1α,25-Dihydroxy-24,24-difluoro-19-norvitamin D$_3$ (6): UV (in EtOH) λ$_{max}$ 260.0, 251.0, 243.0 nm; $^1$H NMR (500 MHz, CD$_3$OD) δ 6.22 (1H, d, J=11.2 Hz, 6-H), 5.90 (1H, d, J=11.2 Hz, 7-H), 4.04 and 3.99 (2H, m, 1β-H and 3α-H), 2.85 (1H, dd, J=13.5, 5.0 Hz, 10β-H), 2.60 (1H, dd, J=13.5, 4.0 Hz, 9β-H), 2.41 (1H, dd, J=13.5, 3.5 Hz, 4α-H), 2.21 (1H, dd, J=13.5, 7.5 Hz, 4β-H), 2.17 (1H, dd, J=13.5, 6.5 Hz, 10α-H), 1.25 (6H, s, 26-H$_3$, 27-H), 0.89 (3H, d, J=7.0 Hz, 21-H$_3$), 0.59 (3H, s, 18-H$_3$); $^{13}$C NMR (125 MHz, CD$_3$OD) δ 141.96 (0, C-8), 133.92 (0, C-5), 126.80 (t, $^1J_{FC}$=247.0 Hz, CF$_2$), 123.42 (1, C-6), 117.21 (1, C-7), 73.70 (t, $^2J_{FC}$=27.5 Hz, C-25, 0), 67.97 (1), 67.69 (1), 57.48 (1), 57.31 (1), 46.81 (0), 45.39 (2), 42.64 (2), 41.74 (2), 37.62 (2), 36.70 (1), 29.81 (2), 28.60 (t, $^2J_{FC}$=24.5 Hz, 2), 27.73 (2), 24.52 (2), 23.89 (3), 23.86 (3), 23.16 (2), 19.00 (3), 12.62 (3); MS (EI) m/z 444 (6, M$^+$), 426 (3, M$^+$-H$_2$O), 393 (2), 341 (2), 313 (6), 269 (5), 251 (6), 199 (6), 191 (15), 161 (10), 145 (19), 111 (43), 107 (100), 89 (80), 79 (78), 75 (43); $^{19}$F NMR (376 MHz, CDCl$_3$) δ−114.9 (dd, J=28.6, 9.7 Hz), −115.6 (dd, J=28.6, 9.7 Hz), −115.8 (dd, J=28.6, 9.7 Hz), −116.5 (dd, J=28.6, 9.7 Hz); MS (EI) m/z 440 (6, M$^+$), 336 (5), 275 (4), 268 (6), 224 (5), 182 (50), 164 (16), 148 (100), 121 (18), 91 (12), 83 (14), 77 (8); MS (ESI) m/z 463 (11, [M+Na]$^+$), exact mass (ESI) calculated for $C_{26}H_{42}O_3F_2Na$ [M+Na]$^+$ 463.2995, found 463.2989.

REFERENCES 1. (a) Bouillon, R.; Okamura, W. H.; Norman, A. W. Structure-function relationships in the vitamin D endocrine system. *Endocr. Rev.*, 1995, 16, 200-257. (b) Jones, G.; Strugnell, S. A.; DeLuca, H. F. Current understanding of the molecular actions of vitamin D. *Physiol. Rev.* 1998, 78, 1193-1231. (c) De Luca, H. F. Overview of general physiologic features and functions of vitamin D. *Am. J. Clin. Nutr.* 2004, 80 (suppl), 1689S-1696S. (d) Feldman, D.; Pike, J. W.; Adams, J. S. Eds. *Vitamin D*, 3$^{rd}$ ed.; Elsevier Academic Press: San Diego, Calif. 2011.

2. (a) Beckman, M. J.; Tadikonda, P.; Werner, E.; Prahl, J.; Yamada, S.; DeLuca, H. F. Human 25-hydroxyvitamin D$_3$-24-hydroxylase, a multicatalytic enzyme. *Biochemistry* 1996, 35, 8465-8472. (b) Akiyoshi-Shibata, M.; Sasaki, T.; Ohyama, Y.; Noshiro, M.; Okuda, K.; Yabusaki, Y. Further oxidation of hydroxycalcidiol by calcidiol 24-hydroxylase. A study with the mature enzyme expressed in *Escherichia coli*. *Eur J. Biochem.* 1994, 224, 335-343. (c) Miyamoto, Y.; Shinki, T.; Yamamoto, K.; Ohyama, Y.; Iwasaki, H.; Hosotani, R.; Kasama, T.; Takayama, H.; Yamada, S.; Suda, T. 1α,25-dihydroxyvitamin D$_3$-24-hydroxylase (CYP24) hydroxylates the carbon at the end of the side chain (C-26) of the C-24-fluorinated analog of 1α,25-dihydroxyvitamin D$_3$. *J. Biol. Chem.* 1997, 272, 14115-14119.

3. (a) Inaba, Y.; Abe, E.; Okuno, S.; Nishizawa, Y.; Yukioka, K.; Otani, S.; Matsui-Yuasa, I.; Morisawa, S.; DeLuca, H. F.; Morii, H. Biological activity of fluorinated vitamin D analogs at C-26 and C-27 on human promyelocytic leukemia cells, HL-60. *Arch. Biochem. Biophys.* 1987, 258, 421-425. (b) Iwasaki, H.; Hosotani, R; Miyamoto, Y.; Nakano, Y. Stereoselective synthesis and structural establishment of (25S)-24,24-difluoro-1α,25,26-trihydroxyvitamin D$_3$, a major metabolite of 24,24-difluoro-1α,25-dihydroxy-vitamin D$_3$. *Tetrahedron* 1998, 54, 14705-14724.

4. (a) Bèguè J. P., Bonnet—Delpon D. Bioorganic and medicinal chemistry of fluorine. John Wiley & Sons, Inc. 2008. (b) Ojima I. Fluorine in medicinal chemistry and chemical biology. John Wiley & Sons, Inc. 2009.

5. (a) Fujishima, T.; Fujii, S.; Harayama, T. Synthesis and biological activity of fluorinated vitamin D. *Curr. Org. Chem.* 2010, 14, 962-976.

6. Brommage, R.; DeLuca H. F. Evidence that 1,25-dihydroxyvitamin D$_3$ is the physiologically active metabolite of vitamin D$_3$. *Endocrine Rev.* 1985, 6, 491-511.

7. Kobayashi, Y., Taguchi, T., Mitsuhashi, S., Eguchi, T., Ohshima, E., Ikekawa, N. Studies on organic fluorine compounds. XXXIX. Studies on steroids. LXXIX. Synthesis of 1α,25-dihydroxy-26,26,26,27,27,27-hexafluorovitamin D$_3$. *Chem. Pharm. Bull.* 1982, 30, 4297-4303.

8. Tanaka, Y., DeLuca, H., Kobayashi, Y., Ikekawa, N. 26,26,26,27,27,27-hexafluoro-1,25-dihydroxyvitamin D$_3$: a highly potent, long-lasting analog of 1,25-dihydroxyvitamin D$_3$. *Arch. Biochem. Biophys.* 1984, 229, 348-354.

9. (a) Posner, G. H.; Wang, Q.; Han, G.; Lee, J. K.; Crawford, K.; Zand, S.; Brem, H.; Peleg, S.; Dolan, P.; Kensler, T. Conceptually new sulfone analogues of the hormone 1α,25-dihydroxyvitamin D$_3$: synthesis and preliminary biological evaluation. *J. Med. Chem.* 1999, 42, 3425-3435. (b) Kensler, T. W.; Dolan, P. M.; Gange, S. J.; Lee, J-K.; Wang, Q.; Posner, G. H. Conceptually new deltanoids (vitamin D analogs) inhibit multistage skin tumorigenesis. Carcinogenesis 2000, 21, 1341-1345.

10. Posner, G. Low—calcemic vitamin D analogs (deltanoids) for human cancer prevention. *J. Nutr.* 2002, 3802S-3803S.

11. Posner, G. H.; Kim, H. J.; Kahraman, M.; Jeon, H. B.; Suh, B. C.; Li, H.; Dolan, P.; Kensler, T. W. Highly antiproliferative, low-calcemic, side chain ketone analogs of the hormone 1α,25-dihydroxyvitamin D$_3$. *Bioorg. Med. Chem.* 2005, 13, 5569-5580.

12. Ikeda, M., Matsumura, H., Sawada, N., Hashimoto, K., Tanaka, T., Noguchi, T., Hayashi, M. Synthesis and biological evaluations of C-23-modified 26,26,26,27,27,27-F$_6$-vitamin D$_3$ analogues. *Bioorg. Med. Chem.* 2000, 8, 1809-1817.

13. (a) Posner, G. H.; Woodard, B. T.; Crawford, K. R.; Peleg, S.; Brown, A. J.; Dolan, P. Kensler, T. W. 2,2-Disubstituted analogues of the natural hormone 1α,25- dihydroxyvitamin D₃: chemistry and biology. *Bioorg. Med. Chem.* 2002, 10, 2353-2365. (b) Peleg, S.; Petersen, K. S.; Suh, B. C.; Dolan, P.; Agoston, E. S.; Kensler, T. W.; Posner, G. H. Low-calcemic, highly antiproliferative, 1-difluoromethyl hybrid analogs of the natural hormone 1α,25-dihydroxyvitamin D₃: design, synthesis, and preliminary biological evaluation. *J. Med. Chem.* 2006, 49, 7513-7517.

14. Yamada, S.; Ohmori, M.; Takayama, H. Synthesis of 24,24-difluoro-25-hydroxyvitamin D₃. *Tetrahedron Lett.* 1979, 21, 1859-1862.

15. Konno, K.; Ojima, K.; Hayashi, T.; Takayama, H. An alternative and efficient synthesis of 24,24-difluoro-1α,25-dihydroxyvitamin D₃. *Chem. Pharm Bull.* 1992, 40, 1120-1124.

16. Flores, A.; Sicifiski, R. R.; Grzywacz, P.; Thoden, J.; Plum, L.; Clagett-Dame, M.; DeLuca, H. F. A 20S combined with a 22R configuration markedly increases both in vivo and in vitro biological activity of 1α,25-dihydroxy-22-methyl-2-methylene-19-norvitamin D₃. *J. Med. Chem.* 2012, 55, 4353-4366.

17. Chiellini, G.; Grzywacz, P.; Plum, L. A.; Barycki, R.; Clagett-Dame, M.; DeLuca, H. F. Synthesis and biological properties of 2-methylene-19-nor-25-dehydro-1α-hydroxyvitamin D₃-26,26-lactones—weak agonists. *Bioorg. Med. Chem.* 2008, 16, 8563-8573.

18. (a) Hallinan, E. A.; Fried, J. 2,2-difluoro-3-hydroxyesters by Reformatskii reaction. *Tetrahedron Lett.* 1984, 25, 2301-2302. (b) Ocampo, R.; Dolbier, Jr. W. R. The Reformatsky reaction in organic synthesis. Recent advances. *Tetrahedron* 2004, 60, 9325-9374. (c) Fiirstner, A. Recent advancements in the Reformatsky reaction. *Synthesis* 1989, 571-590.

19. Posner, G. H.; Lee, J. K.; Wang, Q.; Peleg, S.; Burke, M.; Brem, H.; Dolan, P.; Kensler, T. Noncalcemic, antiproliferative, transcriptionally active, 24-fluorinated hybrid analoges of the hormone 1α,25-dihydroxyvitamin D₃. Synthesis and preliminary biological evaluation. *J. Med. Chem.* 1998, 41, 3008-3014.

20. Molander, G. Application of lanthanide reagents in organic synthesis. *Chem. Rev.* 1992, 92, 29-68. (b) Molander, G. A.; Harris, C. R. Sequencing reactions with samarium (II) iodide. *Chem. Rev.* 1996, 96, 307-338.

21. Barton, D. H. R.; Jang, D. O.; Jaszberenyi, J. Cs. The invention of radical reactions. Part XXIX. Radical mono- and dideoxygenations with silanes. *Tetrahedron* 1993, 49, 2793-2804.

22. (a) Lythgoe, B.; Moran, T. A.; Nambudiry, M. E. N.; Ruston, S.; Tideswell, J.; Wright, P. W. Allylic phosphine oxides as precursors of dienes of defined geometry: synthesis of 3-deoxyvitamin D₂. *Tetrahedron Lett.* 1975, 44, 3863-3866. (b) Lythgoe, B.; Nambudiry, M. E. N.; Tideswell, J. Direct total synthesis of vitamins D₂ and D₃. *Tetrahedron Lett.* 1977, 41, 3685-3688. (c) Lythgoe, B.; Moran, T. A.; Nambudiry, M. E. N.; Tideswell, J. Wright, P. W. Calciferol and its derivatives. Part 22. A direct synthesis of vitamin D₂ and D₃. *J. Chem. Soc., Perkin Trans.* 1 1978, 590-595.

23. Siciński, R. R.; Prahl, J.; Smith, C.; DeLuca, H. F. New 1α,25-dihydroxy-19-norvitamin D₃ compounds of high biological activity: synthesis and biological evaluation of 2-hydroxymethyl, 2-methyl, and 2-methylene analogues. *J. Med. Chem.* 1998, 41, 4662-4674.

24. Shevde, N. K.; Plum, L. A.; Clagett-Dame, M.; Yamamoto, H.; Pike, J. W.; DeLuca, H. F. A potent analog of 1α,25-dihydroxyvitamin D₃ selectively induces bone formation. *Proc. Natl. Acad. Sci. U.S.A.* 2002, 99, 13487-13491.

25. Tavera-Mendoza, L. E.; Quach, T. D.; Dabbas, B.; Hudon, J.; Liao, X.; Palijan, A.; Gleason, J. L.; White, J. H. Incorporation of histone deacetylase inhibition into the structure of a nuclear receptor agonist. *Proc. Natl. Acad. Sci. USA* 2008, 105, 8250-8255.

26. Glebocka, A.; Sichiski, R. R.; Plum, L. A.; Clagett-Dame, M.; DeLuca, H. F. New 2-alkylidene 1α,25-dihydroxy-19-norvitamin D₃ analogues of high intestinal activity: synthesis and biological evaluation of 2-(3'-alkoxypropylidene)- and 2-(3'-hydroxypropylidene) derivatives. *J. Med. Chem.* 2006, 49, 2909-2920.

27. Sheldrick, G. M. 1994, SHELXTL Version 5 Reference Manual, Bruker AXS Inc. (b) *International Tables for Crystallography, Vol. C*, Kluwer: Boston, 1995.

28. Flack, H. D. On enantiomorph—polarity estimation. *Acta Cryst.* A 1983, 39, 876-881.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having the formula:

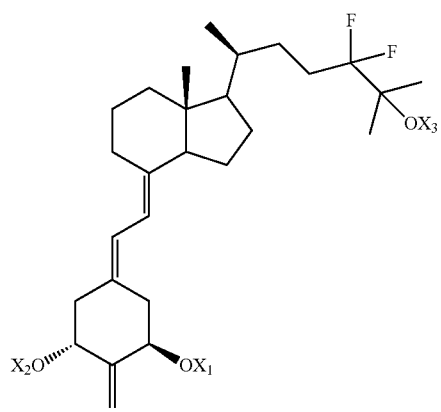

where $X_1$, $X_2$, and $X_3$, which may be the same or different, are each independently selected from hydrogen or a hydroxy-protecting group.

2. The compound of claim 1 wherein $X_1$ is hydrogen.

3. The compound of claim 1 wherein $X_2$ is hydrogen.

4. The compound of claim 1 wherein $X_1$ and $X_2$ are both t-butyldimethylsilyl.

5. The compound of claim 1 wherein $X_3$ is hydrogen.

6. The compound of claim 1 wherein $X_3$ is triethylsilyl.

7. The compound of claim 1 having a formula:
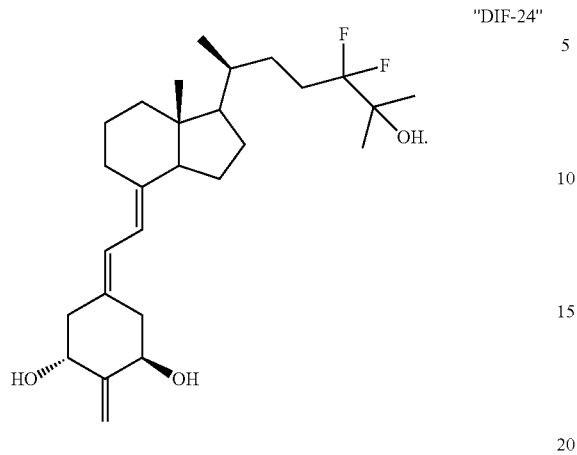
"DIF-24"
8. A pharmaceutical composition containing an effective amount of the compound of claim 1 or a pharmaceutical salt thereof together with a pharmaceutically acceptable excipient.
9. The pharmaceutical composition of claim 8 wherein said effective amount comprises about 1.0 µg to about 1000.0 µg per gram of the composition.
* * * * *

UNITED STATES PATENT AND TRADEMARK OFFICE
CERTIFICATE OF CORRECTION

PATENT NO. : 10,494,337 B2  
APPLICATION NO. : 15/165884  
DATED : December 3, 2019  
INVENTOR(S) : Hector F. DeLuca et al.

It is certified that error appears in the above-identified patent and that said Letters Patent is hereby corrected as shown below:

In the Specification

Column 33, Line 15, "Sicifiski" should be --Siciński--.

Column 33, Line 29, "Fiirstner" should be --Fürstner--.

Column 34, Line 1, "Glebocka" should be --Głębocka--.

Column 34, Line 1, "Sichiski" should be --Siciński--.

Signed and Sealed this  
Twenty-eighth Day of January, 2020

Andrei Iancu  
*Director of the United States Patent and Trademark Office*